(12) United States Patent
Ikeda et al.

(10) Patent No.: US 11,513,007 B2
(45) Date of Patent: Nov. 29, 2022

(54) NOTIFICATION CONTROL DEVICE, NOTIFICATION CONTROL SYSTEM, AND NOTIFICATION CONTROL METHOD

(71) Applicants: Hajimu Ikeda, Kanagawa (JP); Toshihiro Atsumi, Kanagawa (JP); Shotaro Komoto, Kanagawa (JP)

(72) Inventors: Hajimu Ikeda, Kanagawa (JP); Toshihiro Atsumi, Kanagawa (JP); Shotaro Komoto, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 125 days.

(21) Appl. No.: 16/582,366

(22) Filed: Sep. 25, 2019

(65) Prior Publication Data
US 2020/0103286 A1 Apr. 2, 2020

(30) Foreign Application Priority Data

Sep. 28, 2018 (JP) .............................. JP2018-185999
May 27, 2019 (JP) .............................. JP2019-098711

(51) Int. Cl.
*G08B 21/04* (2006.01)
*G01J 5/00* (2022.01)
(Continued)

(52) U.S. Cl.
CPC ............ *G01J 5/0025* (2013.01); *G01V 9/005* (2013.01); *G08B 21/02* (2013.01); *G08B 21/22* (2013.01);
(Continued)

(58) Field of Classification Search
CPC ............ A61G 2203/42; A61G 7/05769; A61G 2203/16; A61G 2203/20; A61G 2203/44; A61G 7/008; A61G 7/018; A61G 7/05; A61G 7/0524; A61G 7/05776; A61G 2203/34; A61H 2201/0142; A61H 2201/5007; A61H 2201/501; A61H 2201/5046; A61H 2201/5048; A61H 23/006; A61H 23/02; A61H 9/0078; G05B 15/02; G05B 19/41815; G05B 2219/45051; G05B 2219/45213; G05B 19/0426;
(Continued)

(56) References Cited

U.S. PATENT DOCUMENTS 6,328,712 B1 * 12/2001 Cartledge ............. A61M 5/142 604/113
8,262,583 B1 * 9/2012 Bryant ................... A63B 23/18 600/529

(Continued)

FOREIGN PATENT DOCUMENTS

JP 2013-211607 10/2013

*Primary Examiner* — Daniel Previl
(74) *Attorney, Agent, or Firm* — IPUSA, PLLC

(57) ABSTRACT

A notification control device for controlling notification based on subject information is disclosed. The subject information including temperature image data, which indicates temperature of a subject captured within a predetermined capturing range, is received. A predetermined destination of notification information, which represents a state of the subject based on the subject information, is notified. A process of notifying the notification information to the predetermined destination is stopped depending on whether or not the subject information includes predetermined identification information.

20 Claims, 16 Drawing Sheets

(51) Int. Cl.
*G01V 9/00* (2006.01)
*G16H 40/20* (2018.01)
*G08B 21/22* (2006.01)
*G08B 25/00* (2006.01)
*G08B 21/02* (2006.01)
*G01J 5/48* (2022.01)

(52) U.S. Cl.
CPC ........... *G08B 25/001* (2013.01); *G16H 40/20* (2018.01); *G01J 5/485* (2022.01); *G01J 2005/0077* (2013.01)

(58) Field of Classification Search
CPC ............... G06F 3/0481; G06F 3/04842; G06F 3/04847; G06F 16/51; G16H 20/30; G16H 40/63; G16H 40/67; G16H 10/60; G16H 40/20; G16H 50/20; G16H 80/00; G16H 15/00; G16H 50/30; G16H 50/70; G16H 20/70; G16H 10/20; G16H 20/13; G16H 10/40; G16H 10/65; G16H 20/17; G16H 20/40; G16H 40/40; G16H 30/20; G16H 30/40; G16H 70/00; G16H 40/60; Y02P 90/02; Y02P 90/08; Y02P 90/04; Y02P 90/16; Y02P 90/28; Y02P 90/80; Y02P 90/86; Y02P 70/50; A61B 2560/0242; A61B 5/4806; A61B 5/486; A61B 2560/0223; A61B 5/1115; A61B 5/6892; A61B 5/0022; A61B 5/002; A61B 5/1117; A61B 5/6891; A61B 5/746; A61B 5/0816; A61B 5/11; A61B 5/1116; A61B 5/4809; A61B 5/7267; A61B 5/7275; A61B 2562/0219; A61B 2562/0247; A61B 5/318; A61B 5/4812; A61B 5/4818; A61B 5/7264; A61B 5/7282; A61B 5/742; A61B 2562/0204; A61B 5/0004; A61B 5/01; A61B 5/02055; A61B 5/024; A61B 5/055; A61B 5/1112; A61B 5/369; A61B 5/389; A61B 5/6803; A61B 7/00; A61B 2505/00; A61B 2562/046; A61B 5/0006; A61B 5/0008; A61B 5/0013; A61B 5/0077; A61B 5/021; A61B 5/0261; A61B 5/053; A61B 5/1118; A61B 5/112; A61B 5/14532; A61B 5/14542; A61B 5/165; A61B 5/447; A61B 5/4815; A61B 5/4833; A61B 5/6806; A61B 5/6807; A61B 5/681; A61B 5/6824; A61B 5/6826; A61B 5/686; A61B 6/0407; A61B 6/0442; A61B 6/0487; A61B 6/102; A61B 6/105; A61B 6/4441; A61B 6/467; A61B 6/54; A61B 6/547; A61B 6/548; A61B 7/04; A61B 7/045; A61B 8/00; A61B 8/06; A61B 8/0808; A61B 8/488; A61B 8/565; A61B 2503/08; A61B 2503/12; A61B 2560/0247; A61B 2560/0252; A61B 2562/029; A61B 5/02; A61B 5/02405; A61B 5/0823; A61B 5/0826; A61B 5/0836; A61B 5/1038; A61B 5/1114; A61B 5/1122; A61B 5/117; A61B 5/1171; A61B 5/14517; A61B 5/14539; A61B 5/14546; A61B 5/14552; A61B 5/1495; A61B 5/18; A61B 5/207; A61B 5/296; A61B 5/4842; A61B 5/4845; A61B 5/4884; A61B 5/6805; A61B 5/6808; A61B 5/6823; A61B 5/6831; A61B 5/685; A61B 5/7285; A61B 5/74; A61B 5/7405; A61B 5/7435; A61B 5/7455; A61B 5/7465; A61B 5/7475; A61B 7/003; A61B 2560/0228; A61B 5/0205; A61B 5/02438; A61B 5/14551; A61B 5/282; A61B 5/291; A61B 5/366; A61B 5/7203; A61B 5/721; A61B 5/7221; A61M 2021/0027; A61M 2021/0083; A61M 2021/0088; A61M 21/02; A61M 2205/18; A61M 2205/3303; A61M 2205/3306; A61M 2205/3368; A61M 2205/3375; A61M 2205/3584; A61M 2205/502; A61M 2205/52; A61M 2205/581; A61M 2205/583; A61M 2205/80; A61M 2230/40; A61M 2230/63; G10L 15/26; G10L 2015/223; G10L 25/78; H04R 2430/01; H04R 29/00; H04R 3/00; H04R 5/04; Y10T 29/5124; Y10T 29/5136; B60P 1/36; B65G 15/30; B65G 2201/042; B65G 2203/042; B65G 43/00; B65G 47/19; B65G 67/22; B65G 67/30; E01C 19/48; E01C 2301/04; G06Q 10/063114; G06Q 10/0832; G06Q 10/0833; G06Q 10/30; G06Q 10/10; G06Q 10/1095; G06Q 20/18; G06Q 20/208; G08B 21/0461; G08B 13/246; Y02W 90/00; Y02W 90/20; A61K 2300/00; A61K 38/26; A61K 38/28; H04L 67/12; H04L 12/282; H04L 51/24; H04L 67/125; H04L 67/22; H04L 12/12; H04L 12/2818; H04L 67/34; H04L 12/2823; H04L 12/2827; H04L 12/2829; H04L 41/069; H04L 43/062; H04L 43/0876; H04L 43/16; H04L 63/0263; H04L 63/083; H04L 63/1408; H04L 63/1425; H04L 63/20; H04L 67/02; H04L 67/025; H04L 67/04; H04L 67/10; H04L 67/26; H04L 67/2823; H04L 67/325; H05K 1/0286; H05K 1/0313; H05K 1/0386; H05K 1/0393; H05K 1/16; H05K 1/189; H05K 2203/178; H05K 3/10; Y04S 20/14; E04H 1/1222; E04H 3/08; H04N 7/141; Y02A 90/10; A61N 2005/1074; A61N 5/103; G06T 2207/20221; G06T 5/50; G07G 1/0045; G07G 1/0054; H04W 4/021; H04W 4/029; H04W 4/80; H04W 4/90
USPC .... 340/539.12, 539.13, 539.22, 539.32, 555, 340/568.1, 572, 1, 636.18, 686.6, 691.6, 340/692
See application file for complete search history.

(56) References Cited

U.S. PATENT DOCUMENTS

| | | | | |
|---|---|---|---|---|
| 2003/0204909 A1* | 11/2003 | Lane | ...................... | A61B 5/1115 5/424 |
| 2009/0043268 A1* | 2/2009 | Eddy | ................... | A61M 1/0037 604/290 |
| 2010/0286997 A1* | 11/2010 | Srinivasan | ............. | G16H 40/20 705/2 |
| 2013/0046543 A1* | 2/2013 | Kitchens | ............... | H04M 3/493 704/270.1 |
| 2015/0109442 A1* | 4/2015 | Derenne | ................. | H04N 7/185 348/143 |
| 2018/0144307 A1* | 5/2018 | West | ...................... | H04W 4/029 |
| 2018/0294052 A1* | 10/2018 | Fishman | ............... | G16H 10/65 |
| 2019/0043336 A1 | 2/2019 | Ikeda et al. | | |
| 2020/0342983 A1* | 10/2020 | Ogawa | ................... | G16H 40/63 |

* cited by examiner

310

| AREA NAME | CORRESPONDING SMALL AREAS |
|---|---|
| FALLING DETECTION AREA | A1, B1, C1, D1, E1 |
| | A5, B5, C5, D5, E5 |
| ATTENTION AREA A | D2, E2 |
| | D4, E4 |
| ATTENTION AREA B | C3 |
| ATTENTION AREA C | B2, C2 |
| | B4, C4 |
| ⋮ | ⋮ |

| DETECTION PATTERN | NOTIFICATION CONTENTS | TEMPERATURE CHANGE |
|---|---|---|
| PATTERN 1 | LEAVING DETECTION INFORMATION + TEMPERATURE IMAGE DATA | SENSING SUBJECT MOVES FROM OUTSIDE OF DETECTION FRAME TO INSIDE OF DETECTION FRAME |
| PATTERN 2 | FALLING DETECTION INFORMATION + TEMPERATURE IMAGE DATA | 1) SENSING SUBJECT MOVES TO FALLING DETECTION AREA FROM BED<br>2) SENSING SUBJECT STAYS IN FALLING DETECTION AREA MORE THAN OR EQUAL TO PREDETERMINED TIME |
| PATTERN 3 | FALLING ATTENTION INFORMATION + TEMPERATURE IMAGE DATA | SENSING SUBJECT MOVES TO ATTENTION AREA A |
| PATTERN 4 | GETTING-UP ATTENTION INFORMATION + TEMPERATURE IMAGE DATA | SENSING SUBJECT MOVES TO ATTENTION AREA B |
| PATTERN 5 | LEAVING ATTENTION INFORMATION + TEMPERATURE IMAGE DATA | SENSING SUBJECT MOVES TO ATTENTION AREA C |
| PATTERN 6 | RETURNING DETECTION INFORMATION + TEMPERATURE IMAGE DATA | SENSING SUBJECT MOVES FROM OUTSIDE OF DETECTION FRAME TO INSIDE OF DETECTION FRAME |
| ... | ... | ... |

| WIRELESS ID | JOB TYPE | AFFILIATION | NAME | ... |
|---|---|---|---|---|
| ID1001 | DOCTOR | INTERNAL MEDICINE | DOCTOR A | ... |
| ... | ... | ... | ... | ... |
| ID2001 | NURSE | PEDIATRICS | NURSE B | ... |
| ... | ... | ... | ... | ... |
| ID3003 | CARE PERSON | SURGERY | CARE PERSON C | ... |
| ... | ... | ... | ... | ... |

NOTIFICATION CONTROL DEVICE, NOTIFICATION CONTROL SYSTEM, AND NOTIFICATION CONTROL METHOD

CROSS-REFERENCE TO RELATED APPLICATION

The present application claims priority under 35 U.S.C. § 119 to Japanese Patent Application No. 2018-185999 filed on Sep. 28, 2018 and No. 2019-098711 filed on May 27, 2019, the entire contents of which are incorporated herein by reference.

BACKGROUND OF THE INVENTION

1. Field of the Invention

The present invention is related to a notification control device, a notification control system, and a notification control method.

2. Description of the Related Art

In facilities such as medical facilities and nursing care facilities, a nursing call system is known for a medical practitioner to be called in response to a calling operation of patients, or the like.

In addition, a nurse call system is known to detect whether a bed is empty or not, and to notify an end of a bed making according to a calling operation when the bed is empty and notify the nurse call according to the calling operation when the bed is not empty (see, for example, Patent Document 1).

PATENT DOCUMENTS

Patent Document 1: Japanese Laid-Open Patent Application No. 2013-211607

SUMMARY OF THE INVENTION

In one aspect of this disclosure, a notification control device for controlling notification based on subject information includes a memory, and a processor coupled to the memory and configured to perform receiving the subject information including temperature image data indicating temperature of a subject captured within a predetermined capturing range; and notifying a predetermined destination of notification information representing a state of the subject based on the subject information, the processor stops a process of notifying the notification information to the predetermined destination depending on whether or not the subject information includes predetermined identification information.

BRIEF DESCRIPTION OF THE DRAWINGS

In the following, embodiments of the present invention will be described with reference to the accompanying drawings.

FIG. 8A and FIG. 8B are diagrams illustrating examples of information managed by the notification control device according to the present embodiment;

DESCRIPTION OF THE PREFERRED EMBODIMENTS

For instance, in such medical facilities, nursing care facilities, and the like, a system may be considered to detect a status of bed users (patients or the like), such as getting out of the bed and returning to bed, by using temperature image data captured by thermo-cameras, or the like installed around the bed, and may inform the nurse call system or the like of a status of the users. For example, the temperature image data may be used to sense temperature and a size of an area corresponding to a user, to estimate a user's condition, and to inform the nurse call system of the user's condition based on estimation results. Thus, for example, it is possible to implement a notification control system, which facilitates securing a privacy of a bed user and detects a status of the user at night after lights are turned off.

However, in this method, after the user has left bed, for example, when a health care worker comes to the bed or the area around the bed, the user may be misidentified as having returned to the bed and notified to the nurse system.

In order to prevent such erroneous detection, it is also possible to assume, for example, that the user has returned to the bed after the temperature and the size of the area corresponding to a person has been detected around the bed and after the user has been moved to the bed and a predetermined period of time has elapsed. However, the method for determining the status of the user over time has a problem in which notification to the nurse call system is delayed in an event of an accident or the like occurring to the bed user.

As described above, in a notification control device that notifies a predetermined destination of the status of the user based on the temperature image data captured within a predetermined capturing range, it has been difficult to reduce an error notification while suppressing a delay of a notification indicating the status of the user.

One embodiment of the present invention will be presented in view of the above-described problems, and in a notification control device that notifies a predetermined destination of a status of a user based on temperature image data captured within a predetermined capturing range, an error notification is reduced while suppressing a delay of a notification indicating the status of the user.

In the following, an embodiment according to the present invention will be described with reference to the accompanying drawings.

System Configuration

Figure 1:
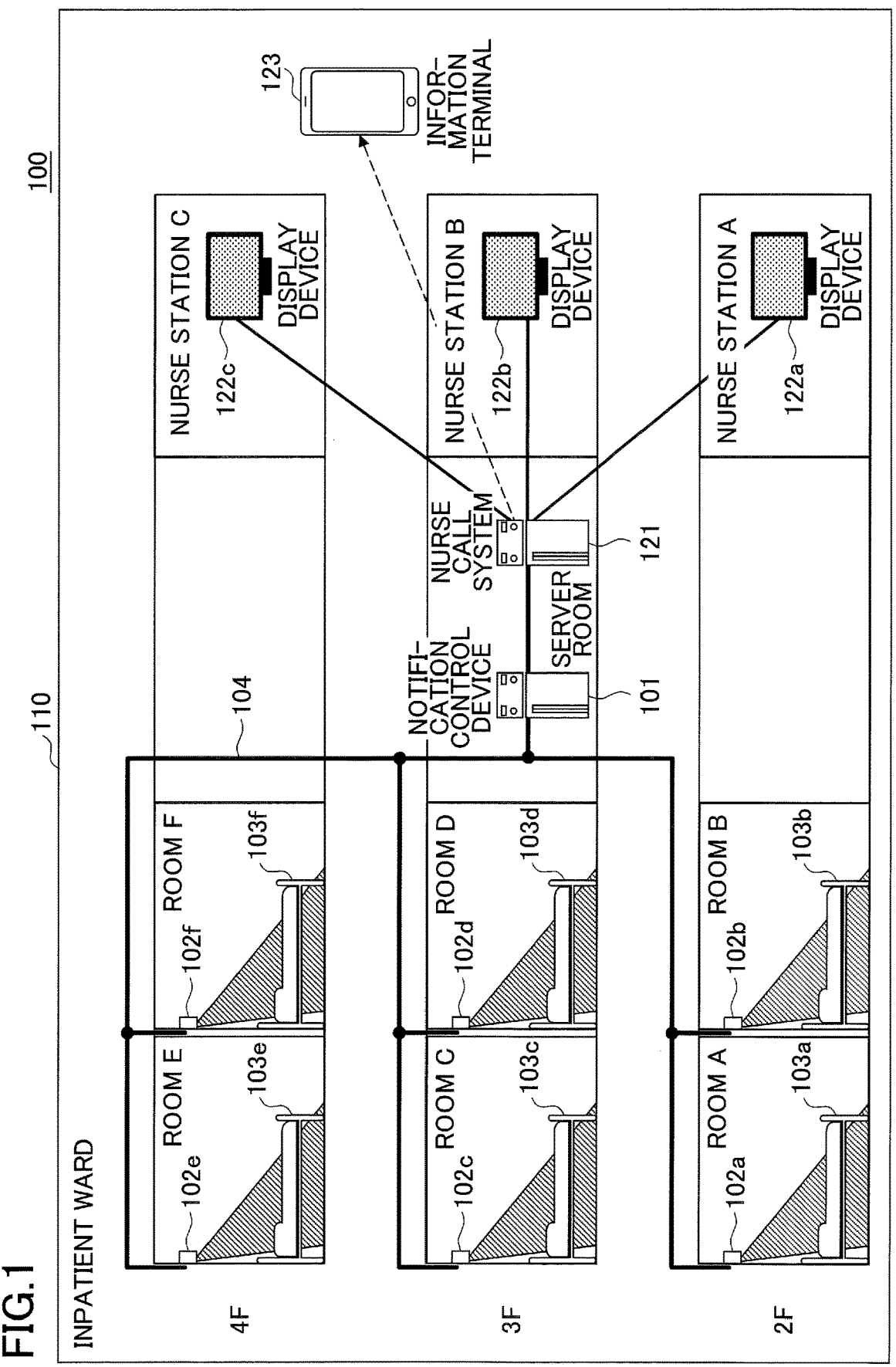
FIG. 1 is a diagram illustrating an example of a system configuration of a notification control system according to an embodiment.

FIG. 1 is a diagram illustrating an example of a system configuration of a notification control system according to an embodiment. The notification control system 100 includes a plurality of information collection devices 102a to 102f installed in an inpatient ward 110, which is an example of a facility such as a medical facility or a nursing facility, and a notification control device 101 communicatively connected to the plurality of information collection devices 102a to 102f via a network 104.

Incidentally, in the following description, when any of the plurality of information collection devices 102a to 102f is represented, the "information collection device 102" is referred to. Further, the number of the information collection devices 102 illustrated in FIG. 1 is an example, and one or more information collection devices 102 may be included in the notification control system 100.

The information collection device 102 includes a short-range wireless module for receiving identification information transmitted from a thermo-camera for capturing temperature image data indicative of a temperature of a subject and a Bluetooth Low Energy (hereinafter referred to as BLE) tag. The information collector 102 may also be referred to as a watch-over camera, simply a camera, or the like.

A thermo-camera is an imaging device that converts infrared radiation from a measurement object to temperature information by imaging the infrared radiation, and visualizes a temperature distribution by color or the like. The thermo-camera is sometimes referred to as a thermographic camera, a thermography, a thermo-vision, a thermo-viewer, or the like.

In the example of FIG. 1, the plurality of information collection devices 102a to 102f are mounted on walls, ceilings, or the like for a plurality of beds 103a to 103f provided in rooms A to F, respectively. For example, the information collection device 102a is mounted on a wall corresponding to the bed 103a provided in the room A and is positioned so as to be able to capture temperature image data representing a temperature of a subject on the bed 103a and around the bed 103a (a predetermined capturing range).

The information collection device 102a photographs the temperature image data of the bed 103a and around the bed 103a at a predetermined frame rate (for example, 5 fps to 1 fps or the like) using the thermo-camera.

In this embodiment, a medical practitioner (for instance, physician, nurse, caregiver, or the like) working at the facility has a BLE tag that transmits identification information identifying the medical practitioner. The information collection device 102a receives identification information (hereinafter, referred to as a wireless ID) transmitted from the BLE tag possessed by the medical practitioner who works in a facility using a short-range radio module (hereinafter, simply referred to as the "medical practitioner").

The medical practitioner may include a variety of staff working at the institution. The temperature image data acquired by the thermo-camera may be image data captured at predetermined time intervals (for example, 10 seconds to 60 seconds). In addition, the short-range wireless module may receive the wireless ID transmitted from a wireless tag other than the BLE tag, such as an active tag of a Radio Frequency Identity (RFID) instead of the BLE tag.

In the above-described configuration, the information collection device 102a transmits user information including captured temperature image data to the notification control device 101 through the network 104. The user information includes identification information for identifying the collection device 102a and the bed 103a (for example, an IP address, a device ID, a bed ID, and the like). When the information collection device 102a receives the wireless ID, the user information includes the received wireless ID.

Similarly, other information collection devices 102b to 102f transmit user information including the temperature image data capturing the bed and the periphery of the bed, the received wireless ID, and the like to the notification control device 101 via the network 104.

The notification control device 101 is regarded as an information processing device having a computer configuration or a system including a plurality of information processing devices. The notification control device 101 receives the user information transmitted from the information collection device 102 and notifies a predetermined destination, such as a nurse call system 121, of the notification information indicating the status of the user who uses the bed based on the received user information.

For example, the notification control device 101 detects a temperature change of a predetermined pattern in one or more sensing regions preset in the capturing range by using the temperature image data included in the user information. Upon detecting the temperature change of a predetermined pattern, the notification control device 101 notifies the nurse call system 121 of the notification information including the notification contents (for example, information indicating the state of the user, the temperature image data, and the like) corresponding to the detected temperature change.

Moreover, the notification control device 101 according to the present embodiment includes a function for stopping a process of notifying the notification information to the nurse call system 121 according to whether or not the user information includes a predetermined wireless ID.

For example, the notification control device 101 detects that a user of the bed 103a has left the bed 103a, by using the temperature image data included in the user information, and sends return information indicating that the user has returned to a predetermined destination when the user returns to the bed 103a. However, with temperature image data, it is difficult to determine whether a person returning is the user using the bed 103a, a medical practitioner, or the like.

Accordingly, as an example, when the received user information includes a pre-registered wireless ID of a medical practitioner or a staff of the facility or a wireless ID of a person from outside of the facility (such as a contracted person allowed to enter such as a cleaner, or the like), the notification control device 101 determines that the person returning is the medical practitioner, or the like, and stops the process of notifying the notification information to the nurse call system 121. By the above described control, it is possible to reduce a possibility that notification to the nurse call system 121 will be erroneously made in a case in which, for example, a bed user of wheelchair returns to the bed 103a with a staff of the facility or in a case of a bed making by a medical practitioner or the like.

As another example, if the received user information does not include the wireless ID of the bed user, the notification control device 101 may determine that the person returning is not the bed user and may stop the process of notifying the notification information to the nurse call system 121.

As another example, the user may attach a BLE tag to a tray or a container used for meals or the like, and even if a user is detected in a predetermined area on a bed as described below, when the received user information includes the wireless ID of the BLE tag, the process of notifying information to the nurse call system 121 may be suspended.

Next, an example will be described that when the user information includes a wireless ID of such as a medical practitioner, a facility employee, or a person from outside of the facility, the notification control device 101 stops the process of notifying the notification information to the nurse call system 121. Wireless IDs of a pre-registered medical practitioner, a facility staff, a person from outside of the facility, and wireless IDs of bed users are examples of predetermined identification information.

The nurse call system 121 is an information processing apparatus including a computer configuration or a system including a plurality of information processing apparatus, and is an example of a predetermined destination to which the notification control apparatus 101 sends the notification information. The nurse call system 121 displays the calling information by a user (for example, a patient, a cared person, or the like) using the bed 103 on display devices 122a to 122c installed in nurse stations A to C, and an information terminal 123 possessed by a staff such as a nurse and a caregiver.

The nurse call system 121 according to the present embodiment is connected to the notification control device 101 through the network 104, and receives notification information that is sent from the notification control device 101 as depicted in FIG. 1. Moreover, the nurse call system 121 may display a display screen for notifying a status of a user on the basis of the received notification information on the display devices 122a to 122c, the information terminal 123, or the like.

A plurality of display devices 122a to 122c are regarded as display devices provided in the nurse stations A to C or the like to display a display screen transmitted from the nurse call system 121.

The information terminal 123 is an information terminal such as a smartphone, a tablet terminal, a notebook, a Personal Computer (PC), or the like possessed by a nurse, caregiver, or the like. The information terminal 123 is able to communicate with the nurse call system 121, for example, by wireless communication, and is able to display a display screen transmitted from the nurse call system 121 by executing a predetermined application.

Arrangement Example of Bed and Camera

Figure 2A:
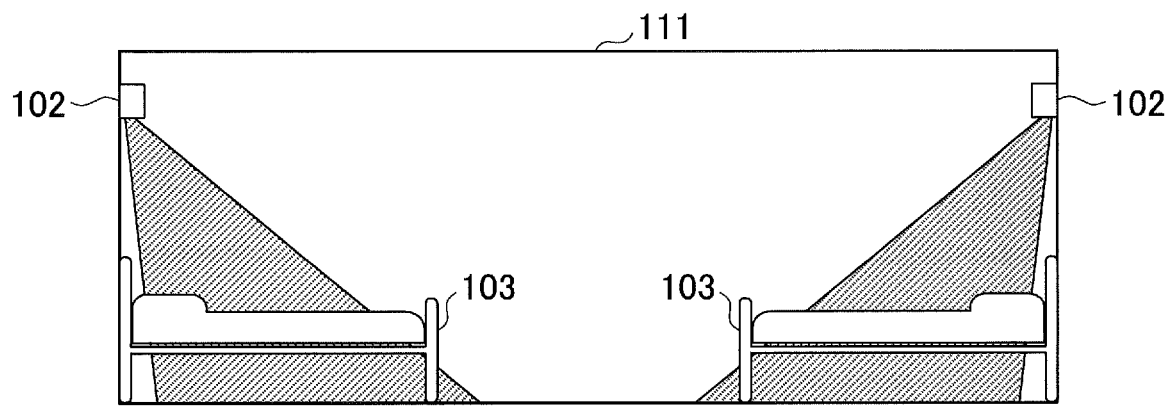
FIG. 2A and FIG. 2B are diagrams illustrating an arrangement example of beds and cameras according to the present embodiment.
Figure 2B:
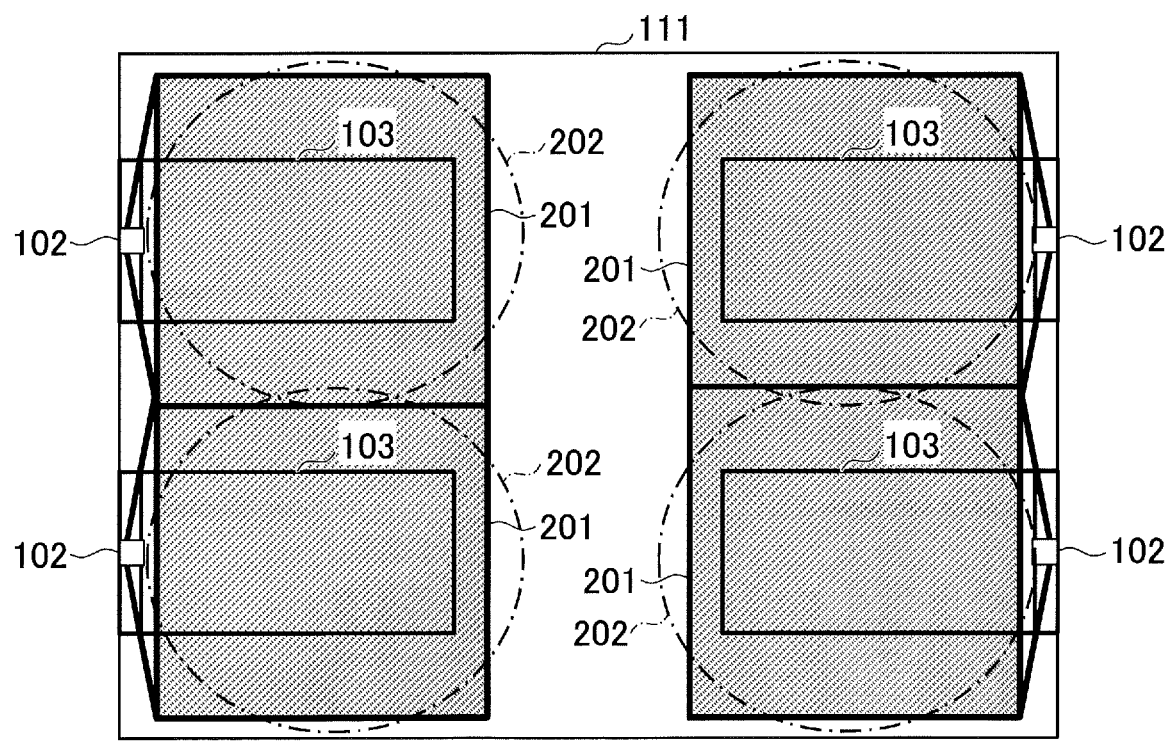

FIG. 2A and FIG. 2B are diagrams illustrating an arrangement example of beds and cameras according to the present embodiment. This embodiment can be applied where a plurality of beds 103 are provided in a room 111, as illustrated in FIG. 2A and FIG. 2B, for example.

For example, as illustrated in FIG. 2A, the information collection device 102 is mounted on a wall or the like in order to acquire image data of the bed 103 and the periphery of the bed 103 corresponding to the information collection device 102. The information collection device 102 may be installed on a ceiling of a room 111.

FIG. 2B illustrates the room 111 viewed from above. The information collection device 102 is positioned so that a thermo-camera is able to be used to capture the temperature image data of a predetermined capturing range 201 including an area of the bed 103 and the periphery of the bed 103 corresponding to the information collection device 102.

In addition, the information collection device 102 is adjusted to be capable of receiving radio waves transmitted by the BLE tag located in a communication range 202 including the bed 103 and a periphery of the bed 103, and of acquiring a wireless ID included in the radio waves by using a short-range radio module.

Each of medical practitioners possesses a BLE tag that transmits the wireless ID identifying the medical practitioner. The BLE tag can control a communication distance by an intensity of the radio wave to be transmitted. For example, the intensity of the radio wave to be transmitted is set so that the communication distance is about 3 m to 4 m.

Example of Detection Area

Figures 3A, 3B:
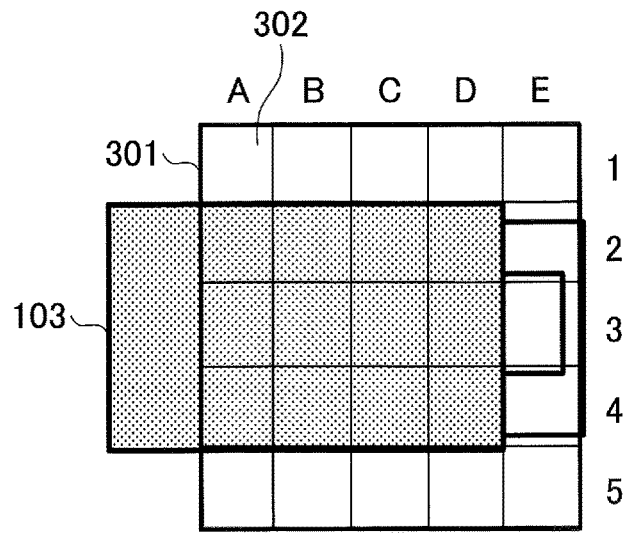
FIG. 3A and FIG. 3B are diagrams for explaining the sensing region according to the present embodiment.

FIG. 3A and FIG. 3B are diagrams for explaining the sensing region according to the present embodiment. The notification control device 101 manages one or more sensing regions preset within the capturing range 201 of the information collection device 102.

For example, a detection frame 301 including a plurality of small areas 302 is set in the capturing range 201 of the information collection device 102 as illustrated in FIG. 3A. In the example of FIG. 3A, there are 25 small areas 302 identified in columns A to E and rows 1 to 5 within the detection frame 301.

As illustrated in FIG. 3B, an attention area B is represented by "C3" indicating a position of a small area. An attention area C is represented by "B2, C2" and "B4, C4" indicating positions of a plurality of small areas. Thereby, the notification control apparatus 101 is able to easily detect a temperature change in one or more sensing regions.

Example of Detection Pattern

FIG. 4A through FIG. 4D are diagrams illustrating examples of detection patterns according to the present embodiment. The notification control device 101 detects a temperature change of a predetermined pattern in one or more sensing regions set in the capturing range 201 by using temperature image data included in user information received from the information collection device 102.

As a preferred example, the notification control device 101 senses a position of a user 401 using the bed 103 by a temperature of a head 402 of the user 401. Of the body of the user 401, the head 402 is less likely to be covered with, for example, clothing or blankets, and the facial portion is less susceptible to an influence of hairs; hence, it is suitable for sensing the position of the user 401.

Figure 4B:
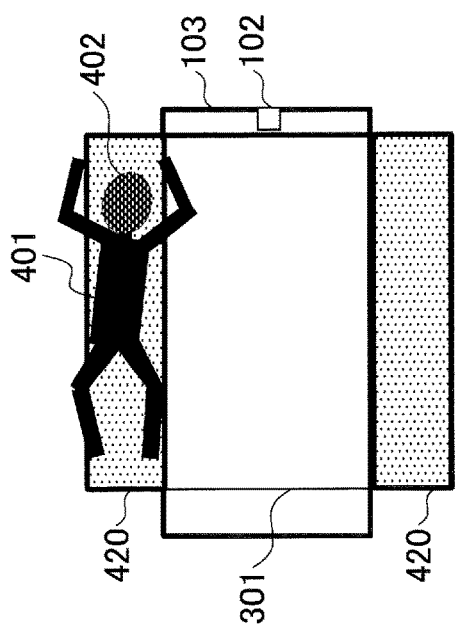
FIG. 4A through FIG. 4D are diagrams illustrating examples of detection patterns according to the present embodiment.
Figure 4A:
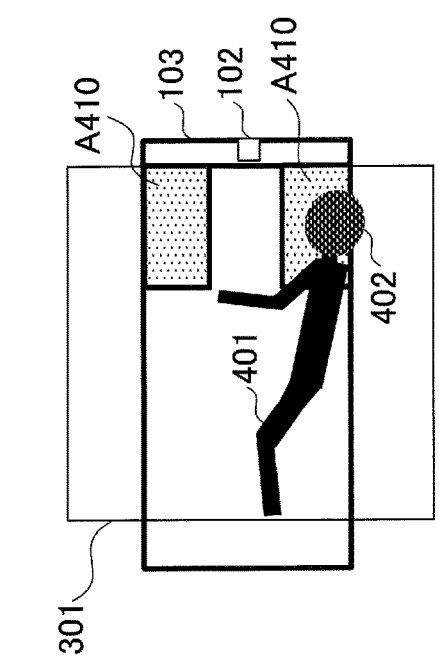

For example, in the temperature image data included in the user information, the head 402 of the user 401 is represented by a different temperature (different color from the other portions) than the other portions, as illustrated in FIG. 4A. Accordingly, the notification control device 101 can detect a position of the user 401 by detecting an area corresponding to a predetermined temperature (for example, 30° C. to 40° C.) and the size of the head 402 from the temperature image data.

In the example of FIG. 4A, as an example of the detection pattern, a detection pattern is shown when the head 402 of the user 401 moves to an attention area A410 defined in FIG. 3A and FIG. 3B. If the head 402 of the user 401 moves to the attention area A410, the notification control device 101 determines, for example, that the user 401 is at risk of falling from the bed 103. In this case, the notification control device 101 notifies the predetermined destination, such as the nurse call system 121, of the notification information indicating that the user 401 is at risk of falling from the bed 103. This notification information includes falling warning information indicating that user 401 may fall from bed 103, a bed ID identifying the bed 103, temperature image data determined to be dangerous, current temperature image data, and the like.

FIG. 4B illustrates another example of the detection pattern in which the user 401 falls from the bed 103. For example, it is assumed that the head 402 of the user 401, which is detected in any of the attention areas A to C defined in FIG. 3A and FIG. 3B, moves to the falling detection area 420 and remains in the falling detection area 420 for a predetermined time. In this case, the notification control device 101 determines that the user 401 has fell from the bed 103. In this case, the notification control device 101 sends the notification information including the falling detection information indicating that the user 401 has fell from the bed, to a predetermined destination such as a nurse call system 121.

Figure 4D:
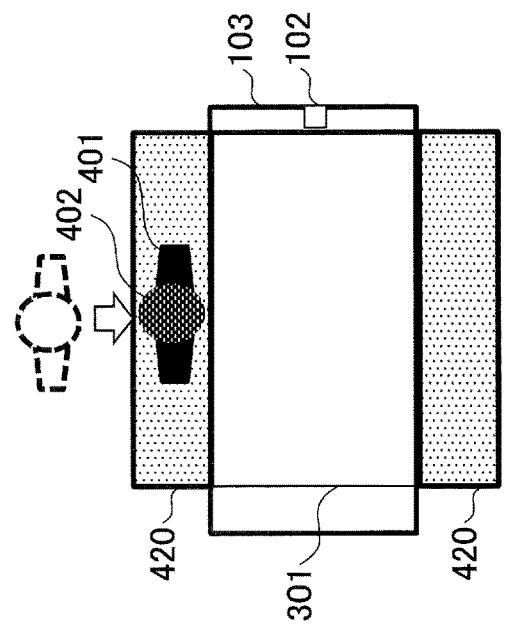
Figure 4C:
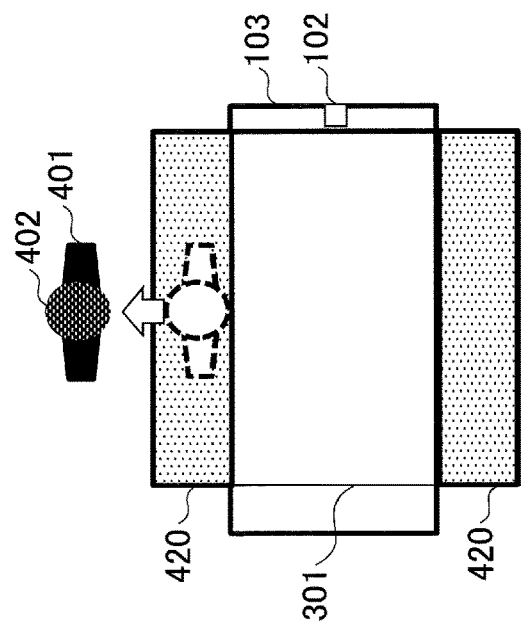

FIG. 4C illustrates another example of a sensing pattern of detection that a user 401 using the bed 103 leaves the bed 103. For example, if the head 402 of the user 401, which was sensed on the bed 103, is detected in the falling detection area 420 and is no longer sensed in the detection frame 301 within a predetermined time, the notification control device 101 determines that the user has been released from bed. In this case, the notification control device 101 sends the notification information including leaving detection information indicating that the user 401 has left the bed 103 to the predetermined destination such as a nurse call system 121.

FIG. 4D illustrates another example of the detection pattern of detecting that the user 401 using the bed 103 returns to the bed 103 (hereinafter referred to as "returning"). For example, suppose a user 401 that was not detected in the detection frame 301 had returned to the bed 103 or around the bed 103. In this case, for example, as depicted in FIG. 4D, the head 402 of the user 401 is sensed in the falling detection area 420. However, with this alone, the notification control device 101 cannot determine whether a person detected in the falling detection area 420 is the user 401 of the bed 103 or a staff of the facility.

Accordingly, the notification control device 101 determines that the person detected in the fall detection area 420 is the user 401 of the bed 103 in a case in which the wireless ID of the medical practitioner is not included in information received from the information collection device 102. The information collection device 102 notifies the predetermined destination such as the nurse call system 121 of the notification information including returning detection information indicating that the user 401 has returned to the bed 103. Meanwhile, when the wireless ID of the medical practitioner is included in the user information received from the information collection device 102, the notification control device 101 determines that the person detected in the fall detection area 420 is the medical practitioner, and stops a process of transmitting the notification information to the predetermined destination.

By the above described control, when the user 401 returning to the bed 103 is collapsed in the fall detection area 420, for example, as depicted in FIG. 4B with hands or feet of the user 401 slipped, the notification control device 101 is able to immediately determine that the user 401 is present in the fall detection area 420. In addition, when a medical practitioner is working in the falling detection area 420 or the like, the notification control device 101 is able to stop the process of transmitting the notification information to the predetermined destination, and thus, it is possible to reduce an error notification to the notification destination.

As described above, according to the present embodiment, in the notification control device 101 that notifies the predetermined destination of a status of a user based on temperature image data captured in the predetermined capturing range 201, it is possible to reduce the error notification while suppressing a delay of a notification indicating the status of the user.

Hardware Configuration

Next, hardware configurations of the notification control device 101 and the information collection device 102 will be described.

Hardware Configuration of Notification Control Device

Figure 5:
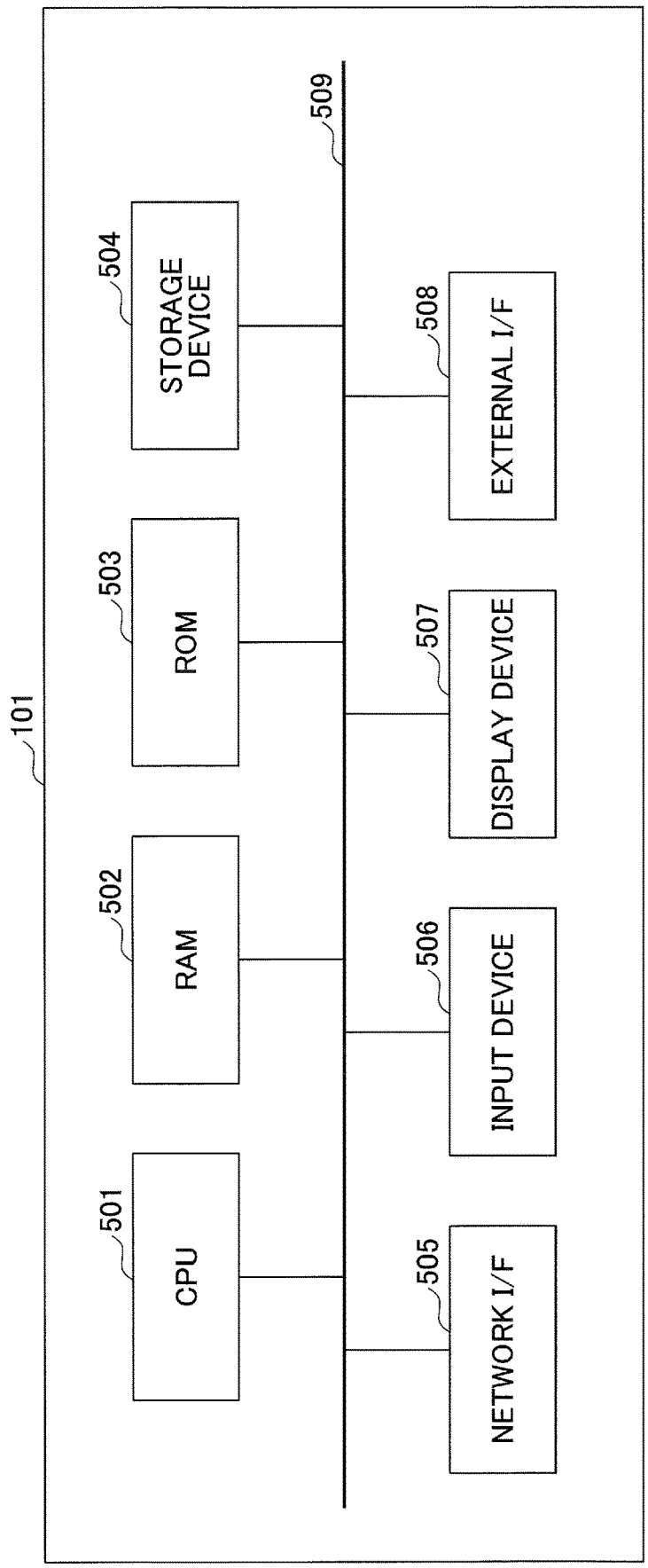
FIG. 5 is a diagram illustrating an example of a hardware configuration of a notification control device according to the present embodiment.

FIG. 5 is a diagram illustrating an example of a hardware configuration of the notification control device according to the present embodiment. The notification control device 101 includes a typical computer configuration such as a Central Processing Unit (CPU) 501, Random Access Memory (RAM) 502, Read Only Memory (ROM) 503, a storage device 504, a network I/F (Interface) 505, an input device 506, a display device 507, an external I/F 508, and a bus 509.

The CPU 501 is an arithmetic unit which realizes functions of the notification control device 101 by reading out a program or data stored in the ROM 503 or the storage device 504 to the RAM 502 and by performing various processes. RAM 502 is a volatile memory used as a work area or the like of CPU 501. ROM 503 is a non-volatile memory which maintains programs and data even when power is turned off.

The storage device 504 may be, for example, a mass storage device such as a hard disk drive (HDD) or a solid state drive (SSD), and stores, for example, an Operating System (OS), application programs, various data, and the like.

The network I/F 505 is a communication interface for connecting the notification control device 101 to the network 104. The input device 506 is a pointing device such as a mouse or an input device such as a keyboard and is used to operate to input various information items to the notification control device 101. The display device 507 is a device to display process results or the like acquired by the notification control device 101.

The external I/F 508 is an interface for connecting external devices. Each of the external devices includes, for example, a recording medium or the like. For example, the notification control device 101 stores a predetermined program in the recording medium and installs the program stored in the recording medium into the notification control device 101 via the external I/F 508, thereby making the predetermined program executable. The bus 509 is connected to each of the above described components (regarded as circuitries) and transmits address signals, data signals, various control signals, and the like.

Hardware Configuration of Information Collection Devices

Figure 6A:
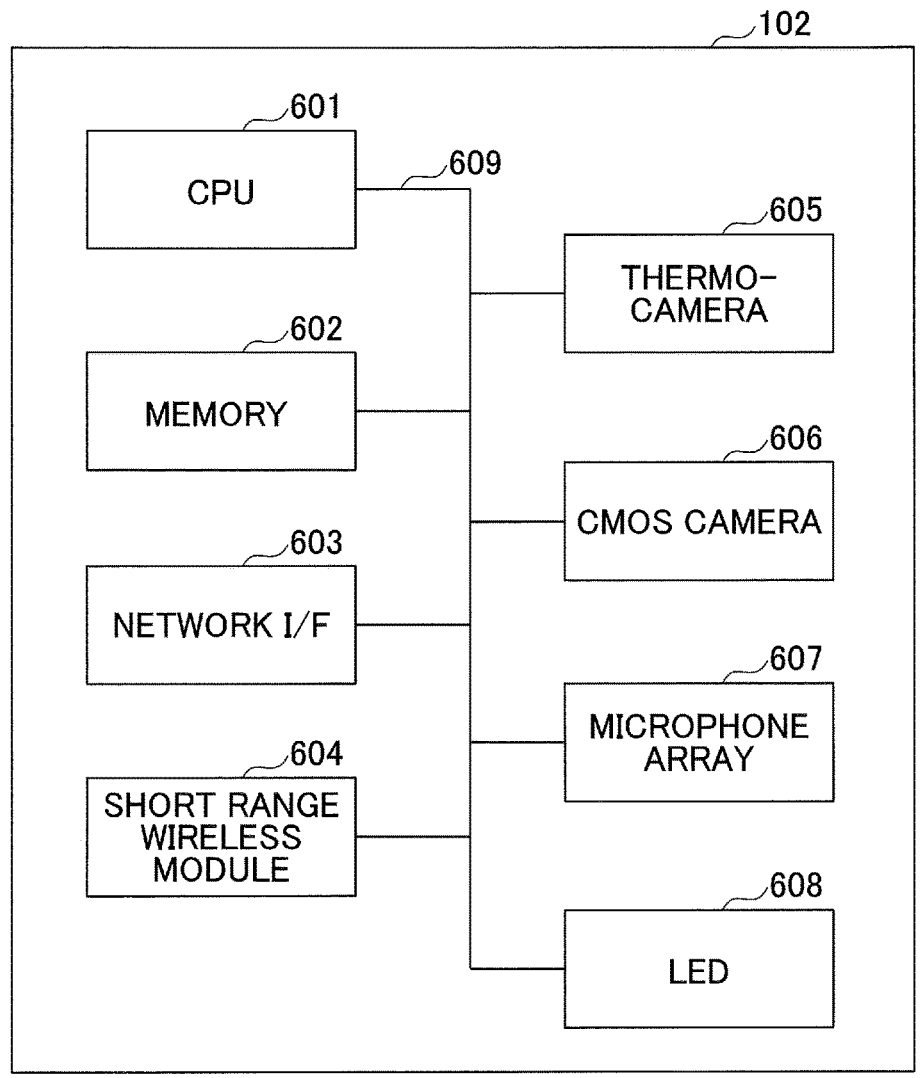
FIG. 6A and FIG. 6B are diagrams illustrating examples of a hardware configuration of an information collection device according to the present embodiment.
Figure 6B:
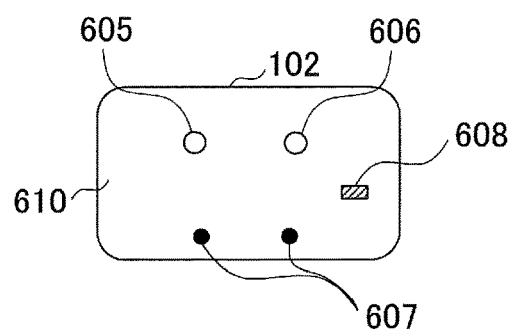

FIG. 6A and FIG. 6B are diagrams illustrating examples of a hardware configuration of the information collection device according to the present embodiment. The information collection device 102 includes a CPU 601, a memory 602, a network I/F 603, a short-range wireless module 604, a thermo-camera 605, a Complementary Metal Oxide Semiconductor (CMOS) camera 606, a microphone array 607, a Light Emitting Diode (LED) 608, and a bus 609, as depicted in FIG. 6A.

The CPU 601 is an arithmetic unit which implements functions of the information collection device 102 by executing a program stored in the memory 602. The memory 602 includes one or more storage devices such as a RAM, a ROM, a flash ROM, and the like. The network I/F 603 is a communication interface for connecting the information collection device 102 to the network 104.

The short-range wireless module 604 includes an antenna, a wireless circuit, and communication control for communicating with a wireless tag such as a BLE tag, for example, by a short-range wireless communication such as BLE communication.

The thermo-camera 605 is an imaging device that converts infrared radiation from a measurement subject to temperature information by imaging the infrared radiation, and visualizes a temperature distribution by color or the like as described in the description of FIG. 1. The thermo-camera 605 is provided in a front panel 610 or the like facing the bed 103, for example, as depicted in FIG. 6B, captures an image within the capturing range 201 including an area of the bed 103 and the periphery of the bed 103, and outputs temperature image data.

The CMOS camera 606 is an imaging device that captures typical photographic data. The CMOS camera 606 is provided on the front panel 610 or the like facing the bed 103, as depicted in FIG. 6B, for example, and captures photographic data in the capturing range 201 including the area of the bed 103 and the periphery of the bed 103, and outputs photographic data taken.

A microphone array 607 selectively acquires a predetermined range of voices by using multiple microphones. The microphone array 607 includes two or more microphones provided on, for example, the front panel 610 opposite the bed 103, as depicted in FIG. 6B, for selectively acquiring voice data at the bed 103 and around the bed 103. As an example, the microphone array 607 acquires audio within the same range as the communication range 202 of the short-range wireless module illustrated in FIG. 2.

The LED 608 is a light emitting element that emits light according to control from the CPU 601. The LED 608 is an example of a display device provided by the information collection device 102 and blinks or illuminates, for example, in a color or a light emitting pattern specified by the CPU 601. The bus 609 is connected to each of the above components and transmits address signals, data signals, various control signals, and the like.

Functional Configuration

Next, a functional configuration of the notification control system 100 will be described.

Figure 7:
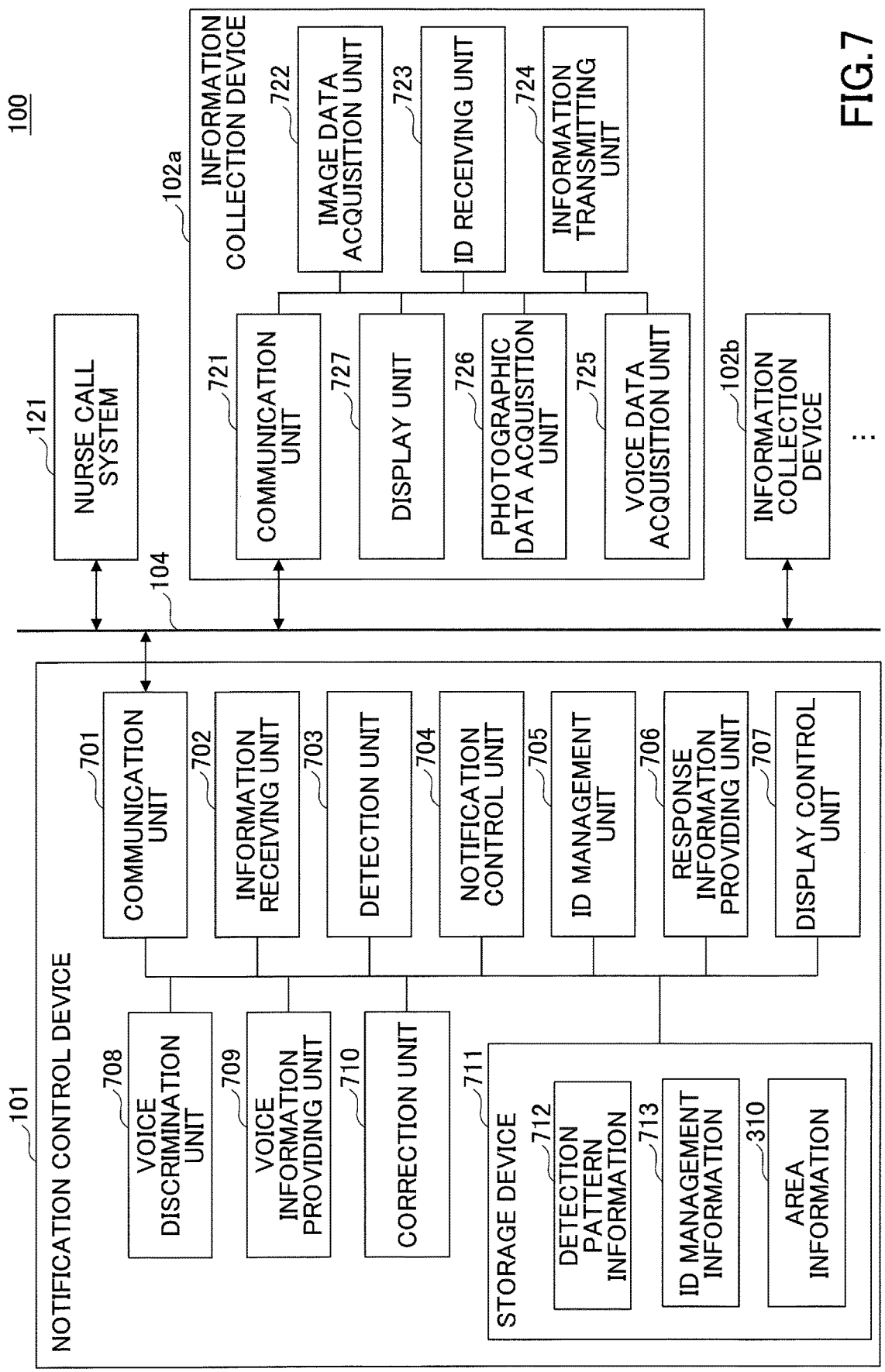
FIG. 7 is a diagram illustrating an example of a functional configuration of a notification control system according to the present embodiment.

FIG. 7 is a diagram illustrating an example of a functional configuration of a notification control system according to the present embodiment. The notification control system 100 includes the notification control device 101 connected to the network 104 and one or more information collection devices 102a, 102b, . . . , and the like. The notification control device 101 is communicatively connected to the nurse call system 121, which is an example of the predetermined destination, for example, through the network 104. In FIG. 7, the information collection device 102b includes the same functional configuration as the information collection device 102a.

Functional Configuration of Notification Control Device

For example, the notification control device 101 realizes a communication unit 701, an information receiving unit 702, a detection unit 703, a notification control unit 704, an ID managing unit 705, a response information providing unit 706, a display control unit 707, a voice discrimination unit 708, a voice information providing unit 709, a correction unit 710, and a storage device 711 by executing a predetermined program in the CPU 501. At least one of the above-described circuitries may be implemented by hardware.

The communication unit 701 is realized, for example, by a program executed in the CPU 501 of FIG. 5 and the network I/F 505. The communication unit 701 connects the notification control device 101 to the network 104 and communicates with the information collection device 102, the nurse call system 121, and the like.

For example, the information receiving unit 702 is implemented by a program executed by the CPU 501 of FIG. 5. The information receiving unit 702 receives user information (subject information) transmitted from the one or more information collection devices 102 through the network 104 and stores the information in the storage device 711.

As described above, the user information includes information for identifying the information collection device 102, the bed 103, or the like, and temperature image data acquired by capturing the capturing range 201 including an area of the bed 103 and the periphery of the bed 103. When the information collection device 102 receives the wireless ID, the user information further includes the received wireless ID.

If necessary, the user information includes voice data acquired by a voice data acquisition unit 725 at the bed 103 and around the bed 103.

The detection unit 703 is implemented, for example, by a program executed in the CPU 501 of FIG. 5. The detection unit 703 detects a temperature change of a predetermined detection pattern in one or more sensing regions preset in the capturing range 201 by using the temperature image data stored in the storage device 711 by the information receiving unit 702.

For example, the notification control device 101 previously stores detection pattern information 712 as depicted in FIG. 8A in the storage device 711 or the like. The detection unit 703 detects the temperature change of the detection pattern set to the detection pattern information 712 in a detection area such as the detection frame 301, the falling detection area, and the attention areas A to C described with reference to FIG. 3A and FIG. 3B.

FIG. 8A is a diagram illustrating an example of the detection pattern information 712 according to the present embodiment. In the example of FIG. 8A, the detection pattern information 712 includes information such as "detection pattern", "notification contents", and "temperature change" as items.

The item "detection pattern" indicates information such as a name, number, or identification information for identifying a detection pattern indicative of a pattern of temperature changes. The item "notification contents" indicates information representing notification contents to be sent to a predetermined destination upon detecting a "temperature change" corresponding to the "detection pattern". The item "temperature change" indicates information representing a change in temperature detected in the detection area such as the detection frame 301, the falling detection area, and the attention areas A to C corresponding to the "detection pattern".

For example, FIG. 8A depicts that the "temperature change" corresponding to the detection pattern "pattern 6" indicates a movement of a sensing target (for example, the head 402 of the user 401) from an outside of the detection frame 301 into the detection frame 301. For example, the detection unit 703 senses a temperature change in the detection frame 301, the falling detection area, and the attention areas A to C. When the sensing target moves from the outside of the detection frame 301 to an inside of the detection frame 301, the detection unit 703 senses a temperature change of "pattern 6" (an example of the predetermined detection pattern).

The notification control unit 704 is implemented by, for example, a program executed by the CPU 501 of FIG. 5. The notification control unit 704 notifies a predetermined destination such as the nurse call system 121 of the notification information representing the state of the user 401 of the bed 103 (the state of the subject), based on user information (information of the subject) received by the information receiving unit 702.

For example, the notification control unit 704 notifies the predetermined destination of the notification information including "notification contents" corresponding to the "detection pattern" when the detection unit 703 detects a temperature change of the predetermined detection pattern and when the user information (subject information) does not include the predetermined wireless ID. Here, the predetermined wireless ID is the wireless ID of the medical personnel working at the facility.

For example, in the detection pattern information 712 illustrated in FIG. 8A, the temperature change of the detection pattern of the "pattern 6" is detected, and the user information does not include the predetermined wireless ID. In this case, the notification control unit 704 notifies the predetermined destination of the notification information including the "notification contents" corresponding to the detection pattern "pattern 6" of the detection pattern information 712 (returning information indicating that a user has returned to a bed and the temperature image data of the bed and the periphery of the bed).

Meanwhile, the notification control unit 704 detects the temperature change of the predetermined detection pattern by the sensing unit 703, and stops the processing of notifying information including "notification contents" corresponding to the "detection pattern" to a predetermined destination when the user information includes a predetermined wireless ID.

For example, the ID management unit (identification information management unit) 705 is implemented by a program executed by the CPU 501 of FIG. 5. The ID management unit (identification information management unit) 705 stores in the storage device 711 or the like and manages the wireless ID identifying the medical practitioner working in the facility.

FIG. 8B is a diagram illustrating an example of the ID management information 713 according to the present embodiment. In the example of FIG. 8B, the ID management information 713 includes information such as "WIRELESS ID", "JOB TYPE", "AFFILIATION", "NAME", and the like as items.

The item "WIRELESS ID" is regarded as identification information included in radio waves transmitted by the BLE tags possessed by a medical personnel working in the facility. The item "JOB TYPE" indicates information representing an occupation of a medical personnel corresponding to the "WIRELESS ID". The item "AFFILIATION" refers to a place to which the medical personnel corresponding to the "WIRELESS ID" belongs. The item "NAME" indicates information representing a name, or the like of the medical personnel corresponding to the "WIRELESS ID".

Using the ID management information 713, the notification control device 101 may determine that a facility staff, a medical practitioner, or the like is near the bed 103 when the wireless ID received at the bed 103 or around the bed 103 is registered in the ID management information 713. When the wireless ID received at the bed 103 and around the bed 103 is not registered in the ID management information 713, the notification control device 101 may determine that the staff of the facility, the medical practitioner, or the like is not near the bed 103.

A response information providing unit (first information providing unit) 706 is realized, for example, by a program executed in the CPU 501 of FIG. 5. The response information providing unit 706 uses the wireless ID included in the user information (subject information) received by the information receiving unit 702 to provide information for visualizing a response of the staff of the facility and the medical practitioner with respect to the user 401 of the bed 103.

For example, the response information providing unit 706 aggregates time at which the wireless ID of each medical practitioner is received in each of the beds 103, and outputs or displays information visualized in tables, graphs, or the like to determine how much time each medical practitioner has spent to respond to the user 401 of each of the beds 103.

The information provided by the response information providing unit 706 may include temperature image data capturing the bed 103 and the periphery of the bed 103. As a result, for example, when the user 401 of the bed 103 is victimized by violence, abuse, or the like, the staff around the bed 103 and their response status are visualized, so that it is possible to expect an effect of preventing violence and abuse by the medical staff.

The display control unit 707 is implemented, for example, by a program executed in the CPU 501 of FIG. 5 and controls a display by a display device such as the LED 608, provided by the information collection device 102.

For example, the display control unit 707 determines whether or not there is a medical practitioner at the bed 103 or around the bed 103 based on the wireless ID included in the information received by the information receiving unit 702. The display control unit 707 sends information indicating that there is a medical practitioner the bed 103 or around the bed 103, as an example to the information collection device 102, when there is a medical practitioner or the like at the bed 103 or around the bed 103. As another example, the display control unit 707 may notify the information collection device 102 of control information indicating that the LED 608 blinks green when a medical practitioner or the like is present at the bed 103 or around the bed 103.

Accordingly, the information collection device 102 flashes green on the LED 608, for example, when there is a medical practitioner at the bed 103 or around the bed 103. The green flashing of the LED 608 is an example of display information indicating that there is a medical practitioner at the bed 103 or around the bed 103.

Meanwhile, when there is no medical practitioner at the bed 103 and around the bed 103, the display control unit 707 notifies the information collection device 102 that there is no medical practitioner at the bed 103 and around the bed 103 as an example. As another example, the display control unit 707 may notify the information collection device 102 of control information indicating that the LED 608 does not blink green when there is no medical practitioner at the bed 103 and around the bed 103.

Accordingly, the information collection device 102 does not cause the LED 608 to blink green when there is no medical practitioner at the bed 103 or around the bed 103.

The voice discrimination unit (discrimination unit) 708 is realized, for example, by a program executed by the CPU 501 of FIG. 5, and determines a type of sound included in the voice data by using the temperature image data and the voice data included in the user information received by the information receiving unit 702.

For example, the speech discrimination unit 708 calculates the sound magnitude of the voice data and analyzes the temperature image data when the sound magnitude is greater than or equal to the first threshold value to calculate an amount of a movement of the user 401 using the bed 103 (for example, an amount of a movement of the head 402 of the user 401).

The voice discrimination unit 708, for example, determines that the type of sound is, for example, a user's groaning, when the magnitude of the sound data is more than or equal to a first threshold value and the amount of the movement of the user is more than or equal to a second threshold value.

However, the voice discrimination unit 708 determines that the type of sound is, for example, a user's snoring, when the magnitude of the sound data is more than or equal to the first threshold value and the amount of movement of the user is less than the second threshold value.

The groaning and the snoring are examples of types of sounds determined by the voice discrimination unit 708. For example, the voice discrimination unit 708 may determine whether or not the type of the sound indicated in the voice data indicates a sound to be notified to the predetermined destination.

The voice information providing unit (second information providing unit) 709 is implemented by a program executed in the CPU 501 of FIG. 5, for example, and outputs or displays information representing a determination result by the voice discriminating unit 708.

Preferably, the information provided by the voice information providing unit 709 includes temperature image data capturing the bed 103 or the periphery of the bed 103. Preferably, the voice information providing unit 709 may output sound acquired at the bed 103 or around the bed 103 in accordance with an operation of an operator.

The correction unit 710 is realized, for example, by a program executed in the CPU 501 of FIG. 5, and corrects a position of the detection frame 301, the falling detection area, and the attention regions A to C set in the capturing range 201 in accordance with a change of a location of the bed 103.

For example, if necessary, the information collection device 102 is able to transmit image data (hereinafter, referred to as photographic data) on which the bed 103 is captured by the CMOS camera 606 to the notification control device 101. The correction unit 710 uses the received photographic data to specify the location of the bed 103 (for example, a contour), and corrects positions of the detection frame 301, the falling sensing area, and the caution regions A to C in accordance with the location of the bed 103.

Preferably, when the correction unit 710 is unable to correct the positions of the detection frame 301, the falling sensing area, and the attention area A to C, the display control unit 707 blinks the LED 608 of the information collection device 102, for example, in red. In this case, the facility staff, the medical practitioner, or the like determines that the bed 103 is not properly positioned, and adjusts the bed 103 to a correct position.

Thereafter, the correction unit 710 again corrects the positions of the detection frame 301, the falling sensing area, and the attention areas A to C, and terminates the red blinking of the LED 608 of the information collection device 102 when the positions are corrected.

The storage device 711 is implemented by, for example, a program executed by the CPU 501 of FIG. 5 and a storage device 504, a RAM 502, or the like, and stores the detection pattern information 712, the ID management information 713, and the area information 310 described above.

Functional Configuration of Information Collection Devices

The information collection device 102 realizes, for example, a communication unit 721, an image data acquisition unit 722, an ID receiving unit 723, an information transmitting unit 724, voice data acquisition unit 725, a photographic data acquisition unit 726, and a display unit 727 by executing a predetermined program in the CPU 601. At least one of the above-described circuitries may be implemented by hardware.

The communication unit 721 is realized, for example, by a program executed in the CPU 601 of FIG. 6A, the network I/F 603, and the like, and communicates with the notification control device 101 and the like by connecting the information collection device 102 to the network 104.

The image data acquisition unit 722 is realized, for example, by a program executed by the CPU 601, and captures the temperature image data of the bed 103 and around the bed 103 by using the thermo-camera 605 of FIG. 6.

The ID receiving unit (identification information receiving unit) 723 is implemented, for example, by a program executed by the CPU 601, and receives a wireless ID from a BLE tag or the like at the bed 103 and around the bed 103 by using the short-range wireless module 604 of FIG. 6.

For example, the information transmitting unit 724 is implemented by a program executed by the CPU 601, and transmits the user information including the temperature image data captured by the image data acquisition unit 722 to the notification control device 101.

The user information includes information that identifies the information collection device 102, the bed 103, or the like, as described above. When the ID receiving unit 723 receives the wireless ID, the information of the user includes the wireless ID received by the ID receiving unit 723. The information transmitting unit 724 may, if necessary, transmit the voice data acquired by the voice data acquisition unit 725, the photographic data acquired by the photographic data acquisition unit 726, or the like to the notification control device 101 included in the user information.

The voice data acquisition unit 725 is implemented, for example, by a program executed by the CPU 601, and acquires the voice data at the bed 103 and around the bed 103 by using the microphone array 607 of FIG. 6.

The photographic data acquisition unit 726 is implemented, for example, by a program executed in the CPU 601 to capture photographic data of the bed 103 and the periphery of the bed 103 by using the CMOS camera 606 of FIG. 6.

The display unit 727 is realized, for example, by a program executed in the CPU 601. The LED 608 of FIG. 6 emits light in a predetermined color, a blinking pattern, or the like to display predetermined information. For example, the display unit 727 flashes green on the LED 608, for example, when there is a staff of the facility, a medical practitioner, or the like at the bed 103 and around the bed 103. When the correction unit 710 of the notification control device 101 cannot correct the position of the detection frame 301, the display unit 727 causes the LED 608 to blink in red as an example.

Process Flow

Next, a process flow of a notification control method according to the present embodiment will be described.

First Embodiment

Notification Control Processing

Figure 9:
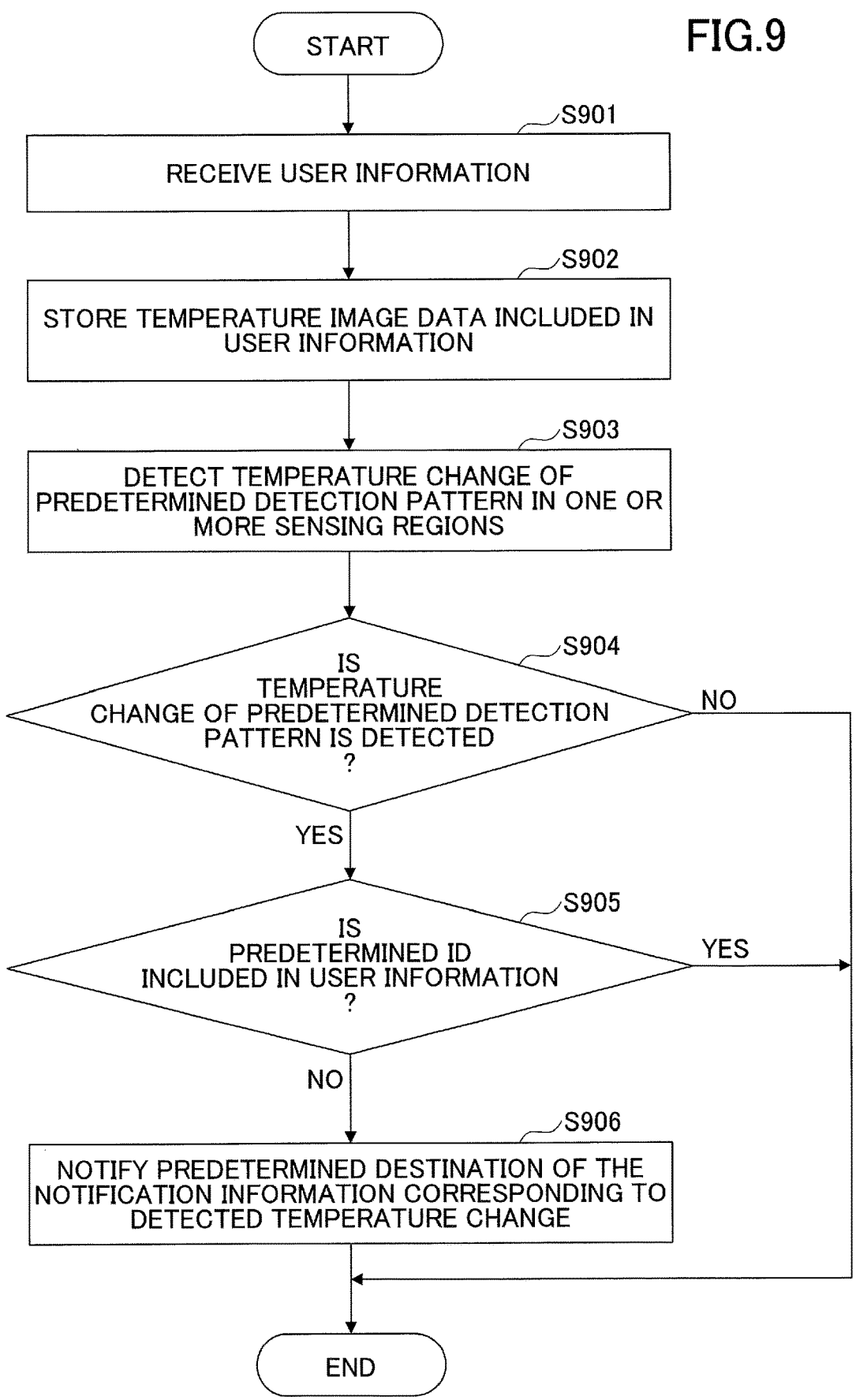
FIG. 9 is a flowchart illustrating an example of a notification control process according to a first embodiment.

FIG. 9 is a flowchart illustrating an example of a notification control process according to a first embodiment. This process in FIG. 9 illustrates an example of the notification control process performed when the notification control device 101 receives user information transmitted from the information collection device 102.

Here, as an example, it is assumed that the information collection device 102 transmits user information including temperature image data capturing the bed 103 and around the bed 103 and the bed ID identifying the bed 103 to the notification control device 101 at a predetermined time interval. When the ID receiving unit 723 receives the wireless ID, the information collection device 102 transmits the user information including the received wireless ID to the notification control device 101.

In step S901, the information receiving unit 702 of the notification control device 101 receives the user information transmitted from the information collection device 102.

In step S902, the information receiving unit 702 stores the temperature image data included in the received user information in the storage device 711.

Preferably, at this time, the information receiving unit 702 deletes the temperature image data after a predetermined storage period from the storage device 711.

In step S903, the detection unit 703 of the notification control device 101 detects a temperature change of a predetermined detection pattern in one or more sensing regions by using the temperature image data stored in the storage device 711.

For example, the detection unit 703 detects the temperature change of the detection pattern set to the detection pattern information 712 in the detection area such as the detection frame 301, the falling detection area, and the attention areas A to C described in FIG. 3A and FIG. 3B.

In step S904, the detection unit 703 of the notification control device 101 determines whether or not the temperature change of the predetermined detection pattern is detected in step S903.

When the temperature change of the predetermined detection pattern is detected, the notification control device 101 advances to step S905. However, when the temperature change of the predetermined detection pattern is not detected, the notification control device 101 terminates this process.

When advancing to step S905, the notification control unit 704 of the notification control device 101 determines whether or not the wireless ID of the medical practitioner is included in the user information received by the information receiving unit 702. For example, when the wireless ID registered in the ID management information 713 is included in the user information received by the information receiving unit 702, the notification control unit 704 determines that the wireless ID of the medical practitioner is included in the user information.

When the wireless ID of the medical practitioner is not included in the user information, the notification control unit 704 advances to step S906. However, when the wireless ID of the medical practitioner is included in the user information, the notification control unit 704 stops the process of notifying the notification information to the predetermined destination and terminates this process.

When advancing to step S906, the notification control unit 704 of the notification control device 101 notifies a predetermined destination such as the nurse call system 121 of the notification information corresponding to the detected temperature change.

By the above-described process, for example, as illustrated in FIG. 4D, when the user 401 using the bed 103 moves into the detection frame 301, it is possible for the notification control unit 704 to immediately notify the predetermined destination of the notification information indicating that the user 401 has returned to the bed 103.

In FIG. 4D, when a person who moved within the detection frame 301 is a medical practitioner, it is possible for the notification control device 101 to abort the process of notifying the notification information to the predetermined destination.

As described above, according to the present embodiment, in the notification control device 101 that notifies the predetermined destination of the status of the user based on the temperature image data captured within the predetermined capturing range, it is possible to reduce the error notification while suppressing the delay of the notification indicating the status of the user.

Display Control Process

Figure 10:
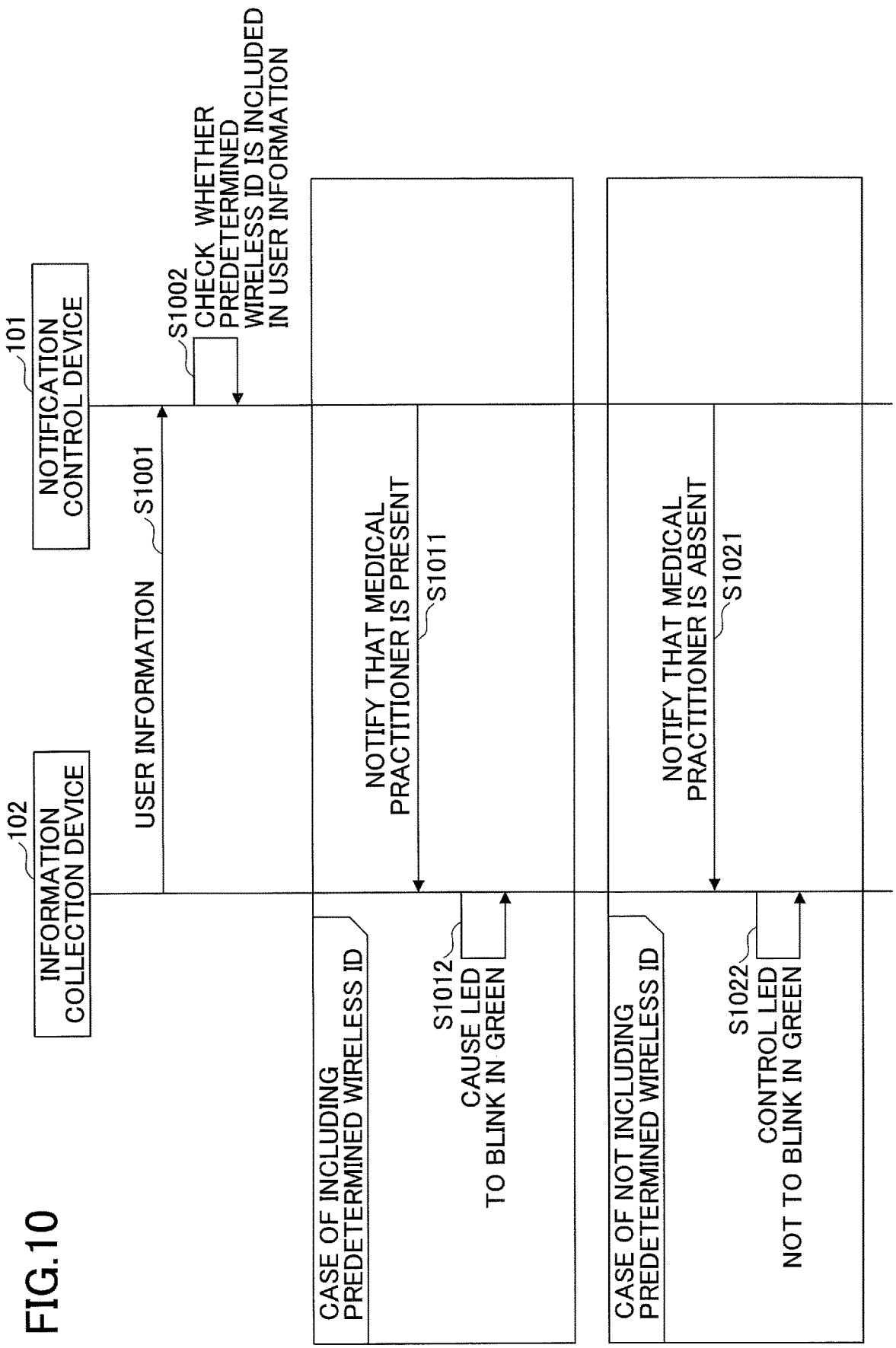
FIG. 10 is a sequence diagram illustrating an example of a display control process according to the first embodiment.

FIG. 10 is a sequence diagram illustrating an example of a display control process according to the first embodiment. This process illustrates an example of the display control process in which the notification control device 101 executes in parallel with the notification control process illustrated in FIG. 9 when the user information transmitted from the information collection device 102 is received.

In step S1001, the information collection device 102 transmits user information including the temperature image data capturing the bed 103 and the periphery of the bed 103 to the notification control device 101.

In step S1002, the display control unit 707 of the notification control device 101 checks whether or not the wireless ID (a predetermined ID) of the medical practitioner is included in the user information received from the information collection device 102.

Here, when the user information includes the wireless ID of the medical practitioner, processes of step S1011 and step S1012 are performed. However, when the user information does not include the wireless ID of the medical practitioner, the processes in step S1021 and step S1022 are performed.

In step S1011, the display control unit 707 of the notification control device 101 notifies the information collection device 102 of information indicating that the medical practitioner is present in the bed 103 or around the bed 103 as an example. As another example, the display control unit 707 may notify the information collection device 102 of control information indicating green blinking of the LED 608.

In step S1012, the display unit 727 of the information collection device 102 blinks the LED 608 in green in response to information indicating that the medical practitioner is present or the control information indicating that the LED 608 blinks green received from the notification control device 101.

However, in step S1021, as an example, the display control unit 707 of the notification control device 101 notifies the information collection device 102 of information indicating that there is no medical practitioner at the bed 103 or around the bed 103. As another example, the display control unit 707 may notify the information collection device 102 of the control information indicating a stop of green blinking of the LED 608.

In step S1022, the display unit 727 of the information collection device 102 does not cause the LED 608 to blink green in response to information received from the notification control device 101 indicating an absence of a medical practitioner or control information indicating a stop of blinking of the LED 608 in green. For example, when the LED 608 is blinking in green, the display unit 727 ends flashing in green. When the LED 608 is not blinking in green, the display unit 727 maintains a present state.

Through the above process, the medical practitioner is able to check the LED 608 of the nearby information collection device 102 and to recognize that the BLE tag is in a fault or out-of-battery state, or that the ID receiving unit 723 of the information collection device 102 is in a fault state in a case in which the LED is not blinking green.

Provision and Processing of Response Information

Figure 11:
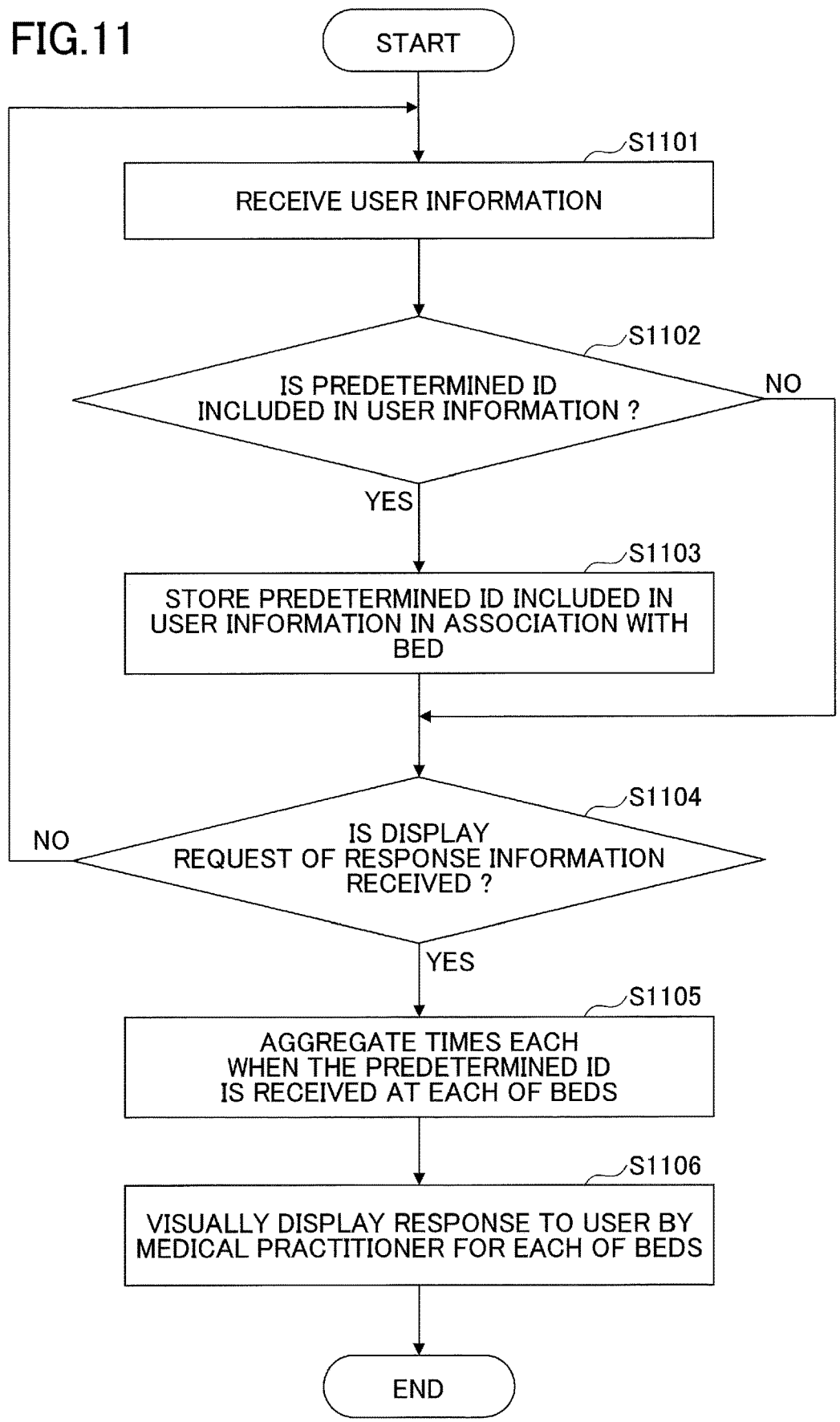
FIG. 11 is a flowchart illustrating an example of a process for providing a response information according to the first embodiment.

FIG. 11 is a flowchart illustrating an example of a process for providing a response information according to the first embodiment. This process represents an example of a process for providing the response information in order to visualize a response of a medical practitioner to the user 401 of the bed 103.

In step S1101, the information receiving unit 702 of the notification control device 101 receives user information transmitted from the information collection device 102.

In step S1102, the response information providing unit 706 of the notification control device 101 determines whether or not a wireless ID (a predetermined ID) of the medical practitioner is included in the received user information.

When the wireless ID of the medical practitioner is included in the user information, the response information providing unit 706 advances to step S1103. However, when the wireless ID of the medical practitioner is not included in the user information, the response information providing unit 706 advances to step S1104.

When advancing to step S1103, the response information providing unit 706 of the notification control device 101 stores the wireless ID of the medical practitioner included in the user information in the storage device 711 in association with the bed 103. For example, the response information providing unit 706 stores in the storage device 711 the wireless ID included in the user information in association with identification information identifying the bed 103, the information collection device 102, or the like.

Preferably, the information stored in the storage device 711 by the response information providing unit 706 is automatically erased after a certain period.

When advancing to step S1104, the response information providing unit 706 of the notification control device 101 determines whether or not a display request of response information is received from the input device 506 or the like.

When the display request of the response information is not received, the notification control device 101 returns the process to step S1101 and executes this process from step S1101 again. However, when the display request of the response information is received, the response information providing unit 706 of the notification control device 101 advances to step S1105.

When advancing to step S1105, the response information providing unit 706 of the notification control device 101 acquires information stored in the storage device 711 and aggregates times each when the wireless ID of the medical practitioner is received at each of beds 103. By this aggregation, for example, a time length, in which the medical practitioner has stayed at each of the beds 103 and around the bed 103, is calculated.

In step S1106, for example, the response information providing unit 706 of the notification control device 101 visually displays the response to the user 401 by a medical practitioner for each of the beds 103.

For example, the response information providing unit 706 creates display information indicating how long it took for the medical practitioner to respond to the user 401 for each of the beds 103 based on the wireless ID of the medical practitioner designated in step S1104, and displays the created display information on the display device 507 or the like.

As a preferred example, in the bed 103 designated in step S1104, the response information providing unit 706 may create display information including the information of the medical practitioner corresponding to the user 401 and the temperature image data, and may display the created display information on the display device 507 or the like. By this process, for example, it is possible to easily specify which medical practitioner made to the user 401 in a case in which the user 401 of the bed 103 was subjected to violence or abuse.

As described above, by the notification control device 101 in accordance with the first embodiment, it is possible to visualize and provide (output, display, or the like) a response to a user 401 of each bed 103 by a medical practitioner.

Second Embodiment

In a second embodiment, an example of a process, which is conducted when voice data at the bed 103 and around the bed 103 are included in user information transmitted by the information collection device 102 to the notification control device 101, will be described.

Sound Discrimination Process

Figure 12:
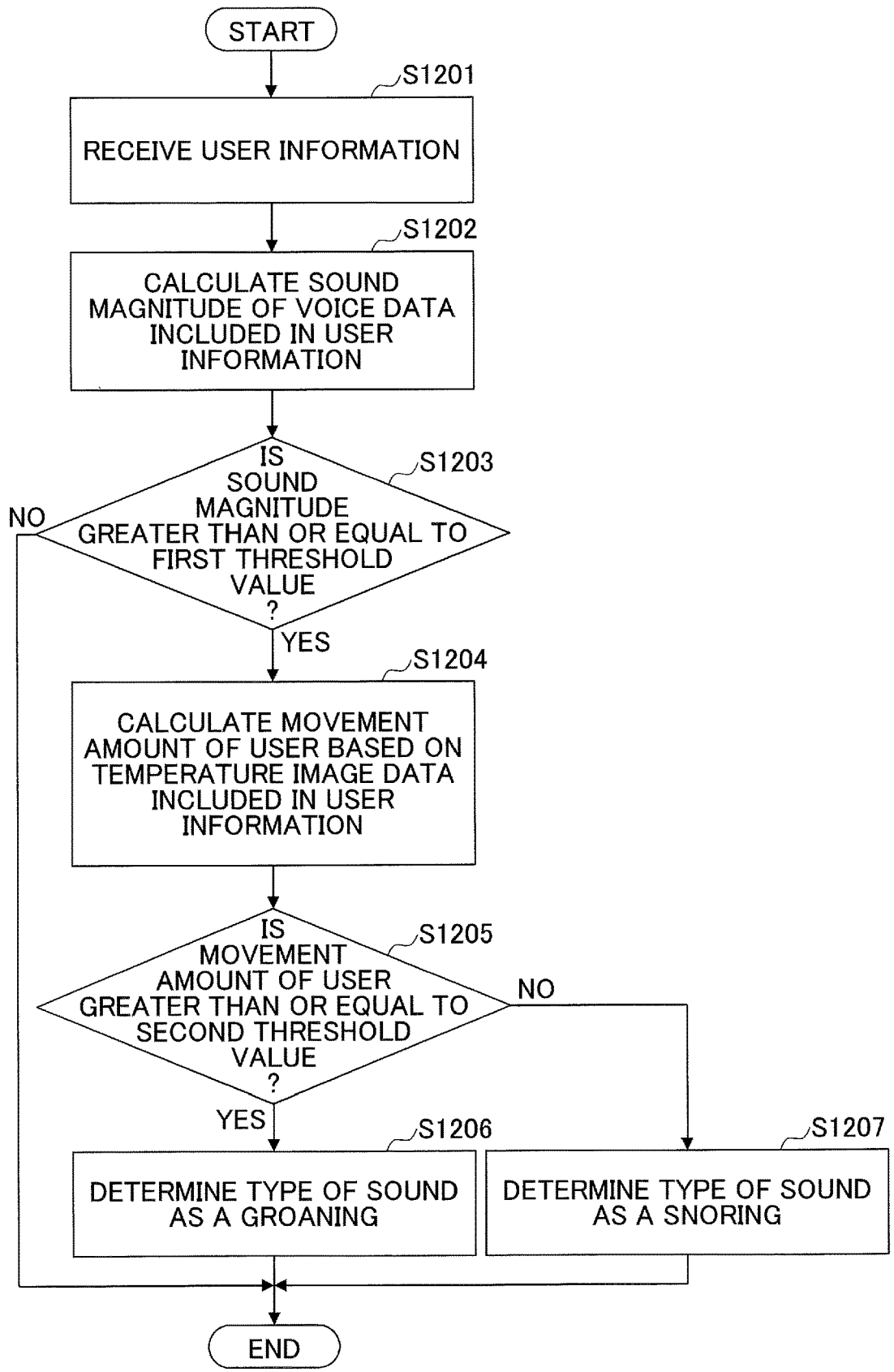
FIG. 12 is a flowchart illustrating an example of a sound discrimination process according to a second embodiment.

FIG. 12 is a flowchart illustrating an example of a sound discrimination process according to a second embodiment. This process illustrates an example of a process in which a voice discrimination unit 708 of the notification control device 101 determines a type of sound around the bed 103 and the bed 103.

In step S1201, the information receiving unit 702 of the notification control device 101 receives user information transmitted from the information collection device 102, and stores the user information in the storage device 711.

In step S1202, the voice discrimination unit 708 calculates a sound magnitude based on the voice data included in the user information.

In step S1203, the voice discrimination unit 708 determines whether or not the sound magnitude in the voice data is greater than or equal to a first threshold value. For example, as the first threshold value, a value for determining whether or not a sound to be discerned is occurred at the bed 103 and around the bed 103 is set beforehand.

When the sound magnitude in the voice data is less than the first threshold value, the voice discrimination unit 708 terminates this process. However, when the sound magnitude in the voice data is greater than or equal to the first threshold value, the voice discrimination unit 708 advances to step S1205.

When advancing to step S1204, the voice discrimination unit 708 calculates a movement amount of the user 401 of the bed 103 (for example, a movement amount of the head 402 of the user 401) using the temperature image data stored in the storage device 711. As an example, the movement amount of the user 401 is represented by a pixel movement amount or the like representing the temperature corresponding to the head 402 of the user 401 in the temperature image data.

In step S1205, the voice discrimination unit 708 determines whether or not the movement amount of the user 401 calculated in step S1204 is more than or equal to a second threshold value. The second threshold is preset, for example, to determine whether the user 401 of the bed 103 is waking or sleeping.

When the movement amount of the user 401 is equal to or greater than the second threshold, the voice discrimination unit 708 determines a type of sound occurring at the bed 103 and around the bed 103, for example, as a groaning (step S1206). However, when the movement amount of the user 401 is less than the second threshold value, the voice discrimination unit 708 determines the type of sound occurring at the bed 103 and around the bed 103, for example, as a snoring (step S1207).

Figure 13:
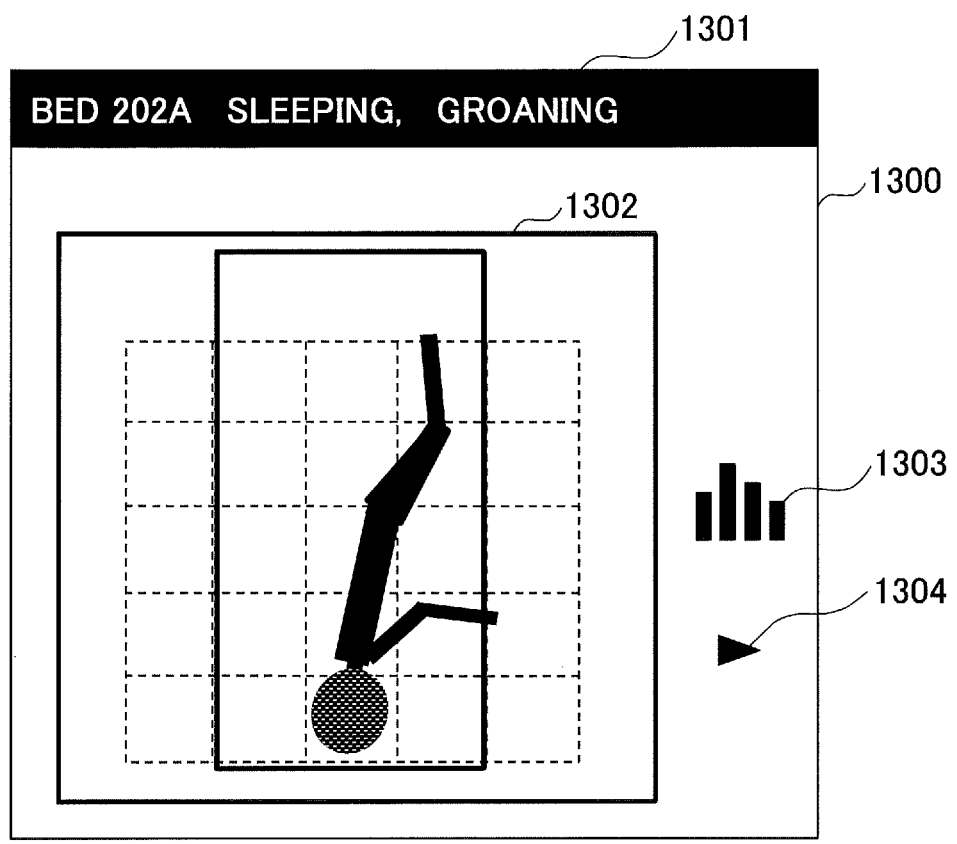
FIG. 13 is a diagram illustrating an example of a display screen according to the second embodiment.

Based on a determination result, for example, the voice information providing unit 709 of the notification control device 101 may display a display screen 1300 as illustrated in FIG. 13 on the display device 507.

Alternatively, the voice information providing unit 709 may notify the display screen 1300 to the nurse call system 121 or the like based on the determination result. For example, the voice information providing unit 709 notifies a predetermined destination such as the nurse call system 121 of the display screen 1300 depicted in FIG. 13 upon determining the type of sound to be a groaning voice in the sound discrimination process depicted in FIG. 12.

FIG. 13 is a diagram illustrating an example of a display screen according to the second embodiment. In the example of FIG. 13, for example, a character string 1301 representing a status of a user 401, a temperature image 1302 captured around the bed 103, a volume information 1303, a play button 1304, and the like are displayed on the picture screen 1300.

For example, as illustrated in FIG. 13, the character string 1301 representing the state of the user 401 displays a bed name identifying the bed 103, the state of the user 401 of the bed 103, and the discrimination result by the sound discrimination process depicted in FIG. 12.

The temperature image 1302 taken around the bed 103 is displayed by using the temperature image data included in the user information received from the information collection device 102.

Volume information 1303 visually indicates the loudness of sound around the bed 103. When the play button 1304 is selected, the voice information providing unit 709 plays back the sound acquired around the bed 103 by using the acquired voice data.

For example, in the first embodiment, when the head 402 of the user 401 is detected in the falling detection area, the attention areas A to C, or the like, the notification control device 101 performs notification process to notify a predetermined destination of notification information indicating a status of the user 401. Therefore, for example, if the head 402 of the user 401 does not move from a position depicted in a temperature image 1302 of FIG. 13, the notification information is not sent.

However, by combining the first embodiment and the second embodiment, for example, even in a case in which the head 402 of the user 401 does not move, the notification control device 101 detects an abnormality of the user 401 and notifies a predetermined destination of an occurrence of the abnormality.

Third Embodiment

In a third embodiment, a process related to a correction of a detection frame 301 by the correction unit 710 of the notification control device 101 will be described.

When the information collection device 102 is installed on a wall or a ceiling of a hospital room, an accuracy of the detection process by the detection unit 703 may be degraded when the location of the bed 103 is displaced from a predetermined position. Therefore, when a position of a bed 103 is misaligned with respect to a detection frame 301 of the information collection device 102, the notification control device 101 includes a correction unit 710 for correcting the position of the detection frame 301 according to the location of the bed 103.

FIG. 14A through FIG. 14D are diagrams for explaining the correction process of the detection frame according to the third embodiment. The information collection device 102 according to the third embodiment includes a function of capturing photographic data of the bed 103 by using the CMOS camera 606 and transmitting the photographic data to the notification control device 101.

For example, the photographic data acquisition unit 726 of the information collector 102 acquires photographic data of the bed 103 and a periphery of the bed 103. The information transmitting unit 724 transmits user information including the temperature image data acquired by the image data acquisition unit 722 and the photographic data acquired by the photographic data acquisition unit 726 to the notification control unit 101.

The information transmitting unit 724 may transmit the photographic data to the notification control unit 101 in addition to the user information. For example, the information collection device 102 may transmit the photographic data to the notification control device 101 upon a request from the notification control device 101 or transmit the photographic data to the notification control device 101 at a predetermined time interval.

Figure 14A:
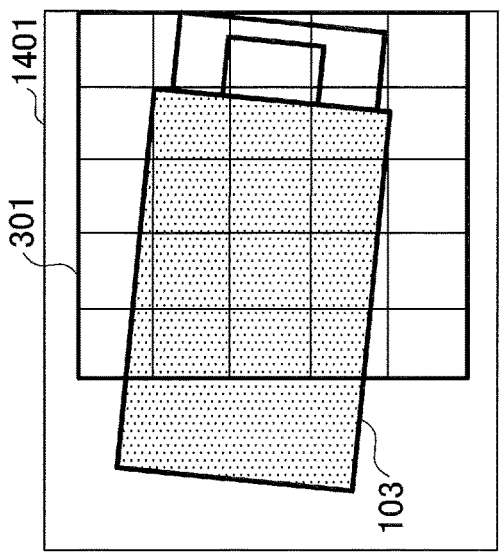
FIG. 14A through FIG. 14D are diagrams for explaining a correction process of a detection frame according to the third embodiment.
Figure 14B:
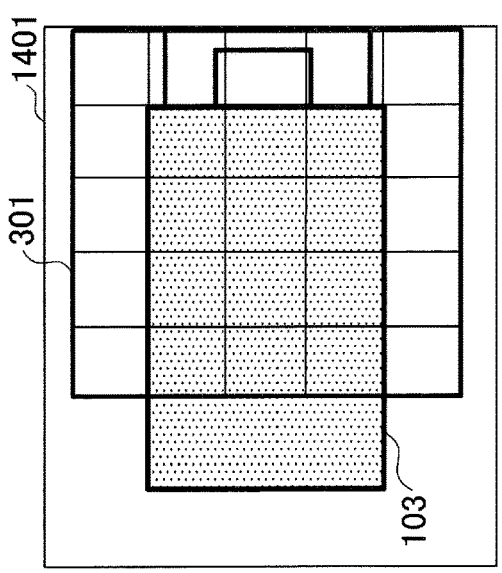

FIG. 14A illustrates an image of a photographic image 1401 and a detection frame 301 when the bed 103 is arranged at a predetermined place. From this state, for example, as illustrated in FIG. 14B, when the location of the bed 103 is displaced, the correction unit 710 of the notification control device 101 detects that a location of the bed 103 has been displaced, for example, by detecting a contour of the bed 103 from the photographic image 1401.

Figure 14C:
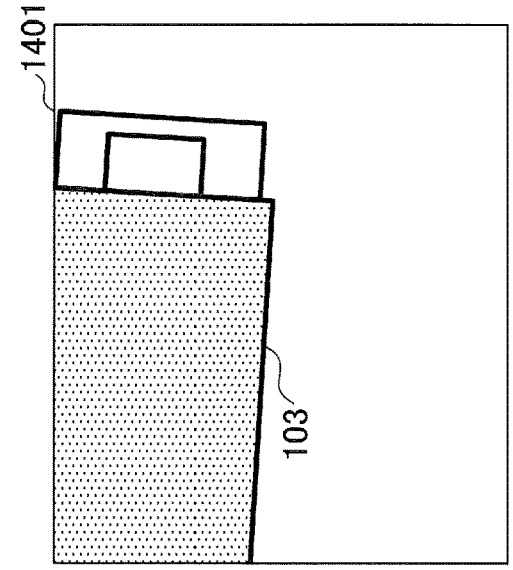

When detecting that the location of the bed 103 is displaced, the correction unit 710 of the notification control device 101 corrects the position of the detection frame 301 according to the contour of the bed 103, for example, as depicted in FIG. 14C.

Figure 14D:
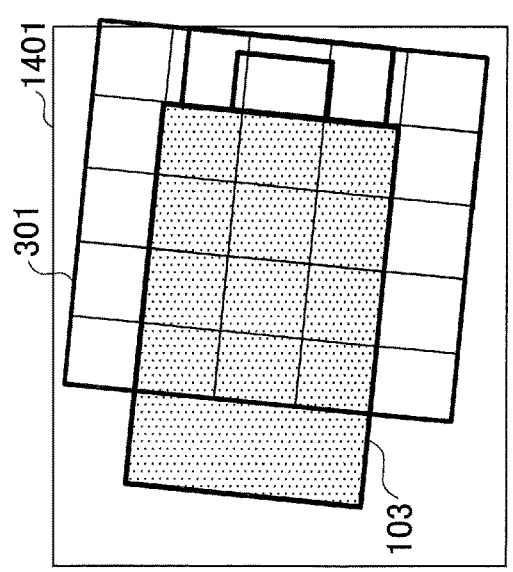

However, as illustrated in FIG. 14D, if the location of the bed 103 is largely displaced, for example, the correction unit 710 of the notification control device 101 does not detect the contour of the bed 103. Moreover, if the location of the bed 103 is largely displaced as described above, even though the contour of the bed 103 is detected, a portion of the detection frame 301 may not be detectable.

In this case, the correction unit 710 of the notification control device 101 notifies that correction of the detection frame 301 cannot be performed, for example, by flashing, in red, the LED 608 of the information collection device 102. Thus, for example, if the LED 608 of the information collection device 102 is flashing red, the medical practitioner around the bed 103 may determine that the location of the bed 103 is displaced and may adjust the position of bed 103. The medical practitioner around the bed 103 may also recognize that the location of the bed 103 is correct if the LED 608 of the information collection device 102 is not blinking in red.

Processing Flow

Figure 15:
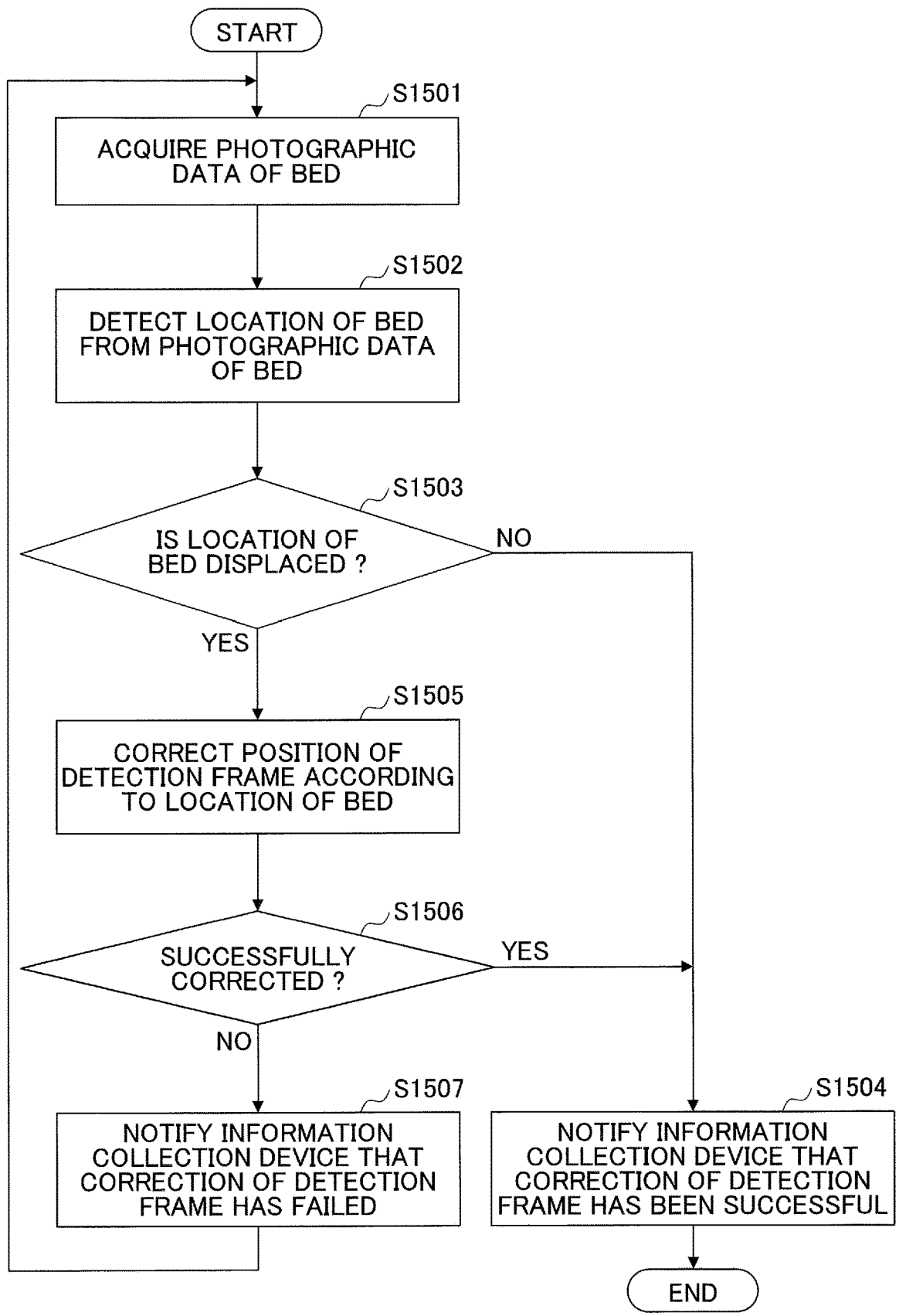
FIG. 15 is a flowchart illustrating an example of the correction process of the detection frame according to the third embodiment.

FIG. 15 is a flowchart illustrating an example of the correction process of the detection frame according to the third embodiment. This process illustrates the example of the correction process of the detection frame performed when the notification control device 101 corrects the detection frame 301.

In step S1501, the correction unit 710 of the notification control device 101 acquires photographic data of the bed 103 transmitted from the information collection device 102. For example, the correction unit 710 acquires the photographic data included in the user information received by the information receiving unit 702.

In step S1502, the correction unit 710 of the notification control device 101 detects a location of the bed 103 from the photographic data of the bed 103. For example, the correction unit 710 analyzes the photographic data and extracts a contour of the bed 103.

In step S1503, the correction unit 710 of the notification control device 101 determines whether or not the location of the bed 103 is displaced with respect to the detection frame 301. For example, as depicted in FIG. 14A, the correction unit 710 determines that the location of the bed 103 is not displaced when the contour of the bed 103 is correctly positioned with respect to the detection frame 301 and the small area 302 within the detection frame 301. However, as depicted in FIG. 14B, the correction unit 710 determines that the location of the bed 103 is displaced with respect to the detection frame 301 and the small area 302 in the detection frame 301 when the contour of the bed 103 is not correctly positioned.

When the location of the bed 103 is not displaced, the correction unit 710 advances to step S1504. However, when the location of the bed 103 is displaced, the correction unit 710 advances to step S1505.

When advancing to step S1504, the correction unit 710 of the notification control device 101 notifies the information collection device 102 that the correction of the detection frame 301 has been successful, and ends this process. Accordingly, when the LED 608 is blinking in red, the information collection device 102 controls the LED 608 to end blinking in red, and when the LED 608 is not blinking in red, the information collection device 102 maintains a state of the LED 608 not blinking in red.

However, when advancing from step S1503 to step S1505, the correction unit 710 of the notification control device 101 corrects the position of the detection frame 301 according to the location of the bed 103, for example, as depicted in FIG. 14C. For example, the correction unit 710 adjusts the detection frame 301 by moving, rotating, enlarging, or reducing the detection frame 301, for the contour of the bed 103 with respect to the detection frame 301 and the small area 302 within the detection frame 301 to be positioned at a correct location.

In step S1506, the correction unit 710 of the notification control device 101 determines whether or not the correction of the detection frame 301 was successful. For example, the correction unit 710 determines that the correction was successful when the detection frame 301 and the small area 302 in the detection frame 301 are detectable as illustrated in FIG. 14C. However, as depicted in FIG. 14D, when the contour of the bed 103 cannot be detected, or when a portion of the small area 302 in the detection frame 301 and the detection frame 301 cannot be detected, the correction unit 710 determines that the correction failed.

When the correction of the detection frame 301 is successful, the correction unit 710 advances to step S1504. However, when the correction of the detection frame 301 fails, the correction unit 710 advances to step S1507.

When advancing to step S1507, the correction unit 710 of the notification control device 101 notifies the information collection device 102 that the correction of the detection frame 301 has failed and returns to step S1501. Accordingly, when the LED 608 is not blinking in red, the information collection device 102 controls the LED 608 to start blinking in red, and when the LED 608 is blinking in red, the LED 608 continues blinking in red.

The above process allows the medical practitioner to easily determine that the bed 103 is displaced and to correct the location of the bed 103.

According to the above described embodiments of the present invention, in a notification control device that notifies a predetermined destination of a status of a user based on temperature image data captured within a predetermined capturing range, it is possible to reduce error notifications while suppressing a delay of a notification indicating the status of the user.

The present invention can be implemented in any convenient form, for example using dedicated hardware, or a mixture of dedicated hardware and software. The present invention may be implemented as computer software implemented by one or more networked processing apparatuses.

The network can comprise any conventional terrestrial or wireless communications network, such as the Internet. The processing apparatuses can comprise any suitably programmed apparatuses such as a general purpose computer, personal digital assistant, mobile telephone (such as a WAP or 3G-compliant phone) and so on. Since the present invention can be implemented as software, each and every aspect of the present invention thus encompasses computer software implementable on a programmable device.

The computer software can be provided to the programmable device using any storage medium for storing processor readable code such as a floppy disk, a hard disk, a CD ROM, a magnetic tape device or a solid state memory device.

The hardware platform includes any desired kind of hardware resources including, for example, a processor such as a central processing unit (CPU), a random access memory (RAM), and a hard disk drive (HDD). The CPU may be implemented by any desired kind of any desired number of processors. The RAM may be implemented by any desired kind of volatile or non-volatile memory. The HDD may be implemented by any desired kind of non-volatile memory capable of storing a large amount of data. The hardware resources may additionally include an input device, an output device, or a network device, depending on the type of the apparatus. Alternatively, the HDD may be provided outside of the apparatus as long as the HDD is accessible. In this example, the CPU, such as a cache memory of the CPU, and the RAM may function as a physical memory or a primary memory of the apparatus, while the HDD may function as a secondary memory of the apparatus.

What is claimed is:

1. A notification control device for controlling notification based on subject information, comprising:
    a memory; and
    a processor coupled to the memory and configured to perform receiving the subject information including temperature image data indicating temperature of a subject captured within a predetermined capturing range, said subject being a user; and
    notifying a predetermined destination of notification information representing a state of the subject based on the subject information,
    wherein, after detecting the subject leaving the predetermined capturing range and subsequently detecting a subsequent subject within the predetermined capturing range, the processor automatically stops a process of notifying the notification information to the predetermined destination upon satisfying a predetermined condition, said predetermined condition being whether it is detected that the subject information of the subsequent subject includes predetermined identification information of another subject that is different from the subject, said another subject being a medical practitioner.

2. The notification control device as claimed in claim 1, wherein the processor further performs
    detecting a temperature change of a predetermined detection pattern in one or more sensing regions preset within the predetermined capturing range by using the temperature image data included in the subject information,
    wherein the processor sends the notification information to the predetermined destination in a case of absence of the identification information in the subject information upon detecting the temperature change of the predetermined detection pattern.

3. The notification control device as claimed in claim 2, wherein the processor stops a process of notifying the notification information to the predetermined destination in a case of presence of identification information in the subject information upon detecting the temperature change of the predetermined detection pattern.

4. The notification control apparatus as claimed in claim 1, wherein the process of notifying the notification information to the predetermined destination is automatically stopped without instructions from a user of the notification control device.

5. The notification control device as claimed in claim 1, wherein
    the predetermined capturing range includes an area including a bed placed in a facility and a periphery of the bed, and
    the subject includes a user using the bed,
    wherein the identification information includes identification information identifying a medical practitioner working at the facility.

6. The notification control device as claimed in claim 5, wherein the processor further performs
    managing the identification information for identifying medical practitioner working in the facility;
    visualizing a response of the medical practitioner to the user of the bed by using the identification information included in the received subject information.

7. The notification control device as claimed in claim 5, wherein the subject information includes voice data collecting a voice at the bed and around the bed, and
    Wherein the processor further performs
    determining a type of sound included in the voice data by using the temperature image data and the voice data included in the subject information, and
    providing information including a determination result and an image indicating temperature at the bed and around the bed.

8. The notification control device as claimed in claim 5, wherein the processor further performs
    correcting a position of one or more sensing regions preset within the predetermined capturing range in accordance with a change in a location of the bed; and
    displaying display information indicating that the position of one or more sensing regions cannot be corrected, on a display unit at the bed or around the bed in a case of unable to correct the position of the sensing area.

9. An information collection device capable of communicating with the notification control device as claimed in claim 5, comprising:
    a memory: and
    a processor coupled to the memory, and the processor configured to perform acquiring temperature image data representing temperature of the bed and a periphery of the bed;
    receiving identification information transmitted by a wireless tag at the bed or around the bed; and
    transmitting subject information including the temperature image data and the identification information to the notification control device upon receiving the identification information.

10. The information collection device as claimed in claim 9, wherein the processor further performs acquiring voice data at the bed and around the bed,
    wherein the subject information includes the voice data.

11. The information collection device as claimed in claim 9, wherein the processor further performs displaying display information indicating that a medical practitioner is present at the bed or around the bed upon determining that the medical practitioner working at the facility is at the bed or around bed.

12. The information collection device as claimed in claim 9, wherein the processor of the notification control device further performs
    correcting a position of one or more sensing regions preset within a predetermined capturing range in accordance with a change in a location of the bed, and
    displaying display information indicating that the position of the one or more sensing regions is unable to be corrected, in a case unable to correct the position of the one or more sensing regions.

13. The notification control device as claimed in claim 1, wherein the subject information further includes identification information related to the subject, and
    wherein the processor stops the process of notifying the notification information to the predetermined destination depending on whether or not the received identification information of the subject matches the predetermined identification information.

14. The notification control device as claimed in claim 1, wherein the identification information is a wireless identification data (ID) of the subject.

15. The notification control device as claimed in claim 1, wherein the wireless identification data (ID) of the subject is transmitted from a Bluetooth Low Energy tag attached to the subject.

16. The notification control device as claimed in claim 1, wherein the predetermined identification information of the another subject is preliminarily stored and managed in a storage unit as a non-target of the process of notifying the notification information to the predetermined destination.

17. The notification control device as claimed in claim 1, wherein the processor automatically stops the process of notifying the notification information to the predetermined destination upon detecting that the subject information of the subsequent subject includes the predetermined identification information after detecting the subject returning to the predetermined capturing range, and
    wherein the processor automatically resumes the process of notifying the notification information to the predetermined destination after detecting the subsequent subject leaving the predetermined capturing range and subsequently determining that the subject information of the subject does not include the predetermined identification information.

18. A notification control system for controlling notification based on subject information, comprising:
    a memory; and
    one or more processors coupled to the memory and configured to perform receiving subject information including temperature image data indicating temperature of a subject captured within a predetermined capturing range, said subject being a user; and
    sending notification information representing a state of the subject to a predetermined destination based on the subject information,
    wherein, after detecting the subject leaving the predetermined capturing range and subsequently detecting a subsequent subject within the predetermined capturing range, the one or more processors automatically stop a process of sending the notification information to the predetermined destination upon satisfying a predetermined condition, said predetermined condition being whether it is detected that the subject information of the subsequent subject includes predetermined identification information of another subject that is different from the subject, said another subject being a medical practitioner.

19. A notification control method executed by a computer that controls notification based on subject information, the method comprising:
    receiving subject information including temperature image data indicating temperature of a subject captured in a predetermined range, said subject being a user; and
    notifying a predetermined destination of notification information indicating a state of the subject based om the subject information,
    wherein the method further comprises, after detecting the subject leaving the predetermined capturing range and subsequently detecting a subsequent subject within the predetermined capturing range, automatically stopping a process of notifying the notification information to the predetermined destination up upon on satisfying a predetermined condition, said predetermined condition being whether it is detected that the subject information of the subsequent subject includes predetermined identification information of another subject that is different from the subject, said another subject being a medical practitioner.

20. A program for causing a computer to execute a notification control method as claimed in claim 19.

* * * * *